US009622895B2

(12) United States Patent
Cohen et al.

(10) Patent No.: US 9,622,895 B2
(45) Date of Patent: Apr. 18, 2017

(54) METHODS AND SYSTEMS FOR LOADING AND DELIVERING A STENT

(71) Applicant: Boston Scientific Scimed, Inc., Maple Grove, MN (US)

(72) Inventors: Adam L. Cohen, Sudbury, MA (US); Manjunath Penagondla, Bangalore (IN); Joshin Sahadevan, Bangalore (IN); Naroun Suan, Lawrence, MA (US); Ra Nam, Lawrence, MA (US); Saroun Suan, Lawrence, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 198 days.

(21) Appl. No.: 14/515,053

(22) Filed: Oct. 15, 2014

(65) Prior Publication Data

US 2015/0105849 A1 Apr. 16, 2015

Related U.S. Application Data

(60) Provisional application No. 61/890,999, filed on Oct. 15, 2013.

(51) Int. Cl.
*A61F 2/966* (2013.01)
*A61F 2/07* (2013.01)
*A61F 2/95* (2013.01)

(52) U.S. Cl.
CPC ............... *A61F 2/966* (2013.01); *A61F 2/07* (2013.01); *A61F 2/95* (2013.01); *A61F 2002/9517* (2013.01); *A61F 2002/9522* (2013.01)

(58) Field of Classification Search
CPC ...... A61F 2002/9528; A61F 2002/9517; A61F 2002/9522; A61F 2002/9511; A61F 2/95;
(Continued)

(56) References Cited

U.S. PATENT DOCUMENTS 5,026,377 A 6/1991 Burton et al.
5,683,451 A 11/1997 Lenker et al.
(Continued)

FOREIGN PATENT DOCUMENTS

EP 0 696 447 A2 2/1996
WO 2010027485 A1 3/2010

*Primary Examiner* — Jocelin Tanner
(74) *Attorney, Agent, or Firm* — Seager, Tufte & Wickhem, LLP

(57) ABSTRACT

Some embodiments of the present disclosure are directed to a stent loading and delivery device, and methods for making and using the device. The device includes a handle assembly and an outer tubular member extending distally from the handle assembly. A proximal end of the outer tubular member is attached to a first handle of the handle assembly. The device includes an intermediate tubular member slidably disposed within the outer tubular member and an inner elongate member extending distally from the handle assembly within the intermediate tubular member. A stent constrainment mechanism is attached to a distal end of the intermediate tubular member and can receive a stent into a distal opening of the stent constrainment mechanism in an expanded state. Upon longitudinal actuation of the outer tubular member the stent constrainment mechanism collapses radially inward around the stent to constrain it within the outer tubular member.

20 Claims, 28 Drawing Sheets

(58) Field of Classification Search
CPC .... A61F 2/07; A61F 2/97; A61F 2/966; A61F 2/962; A61B 17/22012; A61B 17/221; A61B 2017/22035
See application file for complete search history.

(56) References Cited

U.S. PATENT DOCUMENTS

| | | |
|---|---|---|
| 5,800,517 A | 9/1998 | Anderson et al. |
| 6,024,763 A | 2/2000 | Lenker et al. |
| 6,132,458 A | 10/2000 | Staehle et al. |
| 6,149,680 A | 11/2000 | Shelso et al. |
| 6,187,016 B1 | 2/2001 | Hedges et al. |
| 6,355,060 B1 | 3/2002 | Lenker et al. |
| 6,391,050 B1 | 5/2002 | Broome |
| 6,464,683 B1 | 10/2002 | Samuelson et al. |
| 6,514,280 B1 | 2/2003 | Gilson |
| 6,602,280 B2 | 8/2003 | Chobotov |
| 6,902,575 B2 | 6/2005 | Laakso et al. |
| 6,926,732 B2 | 8/2005 | Derus et al. |
| 7,947,070 B2 | 5/2011 | Headley et al. |
| 8,372,133 B2 | 2/2013 | Douk et al. |
| 8,468,667 B2 | 6/2013 | Straubinger et al. |
| 8,668,728 B2 | 3/2014 | Headley et al. |
| 8,998,980 B2 | 4/2015 | Shipley et al. |
| 9,254,371 B2 | 2/2016 | Martin et al. |
| 9,265,639 B2 | 2/2016 | Schneider et al. |
| 2002/0120277 A1* | 8/2002 | Hauschild ............ A61B 17/221 606/108 |
| 2003/0139795 A1 | 7/2003 | Olson |
| 2006/0184226 A1* | 8/2006 | Austin .................... A61F 2/95 623/1.11 |
| 2007/0270932 A1* | 11/2007 | Headley ................. A61F 2/95 623/1.11 |
| 2009/0082840 A1 | 3/2009 | Rusk et al. |
| 2009/0171434 A1 | 7/2009 | Rusk et al. |
| 2011/0082464 A1 | 4/2011 | Douk et al. |
| 2011/0178588 A1 | 7/2011 | Haselby |
| 2011/0264191 A1* | 10/2011 | Rothstein ............ A61F 2/2436 623/1.11 |
| 2012/0172962 A1 | 7/2012 | Nam et al. |
| 2012/0172964 A1 | 7/2012 | Schneider et al. |
| 2013/0110223 A1 | 5/2013 | Munsinger et al. |
| 2013/0123897 A1 | 5/2013 | Robinson |

\* cited by examiner

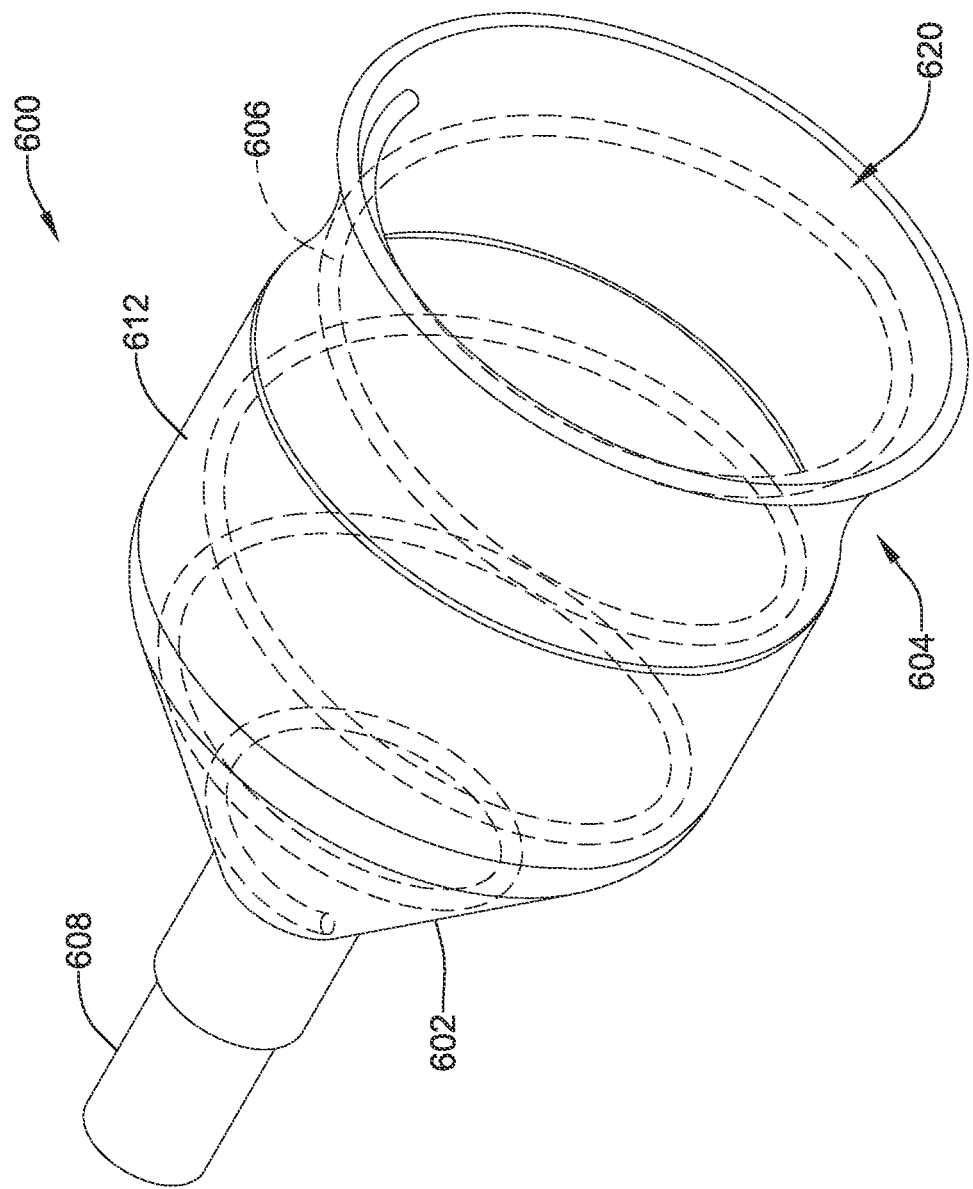

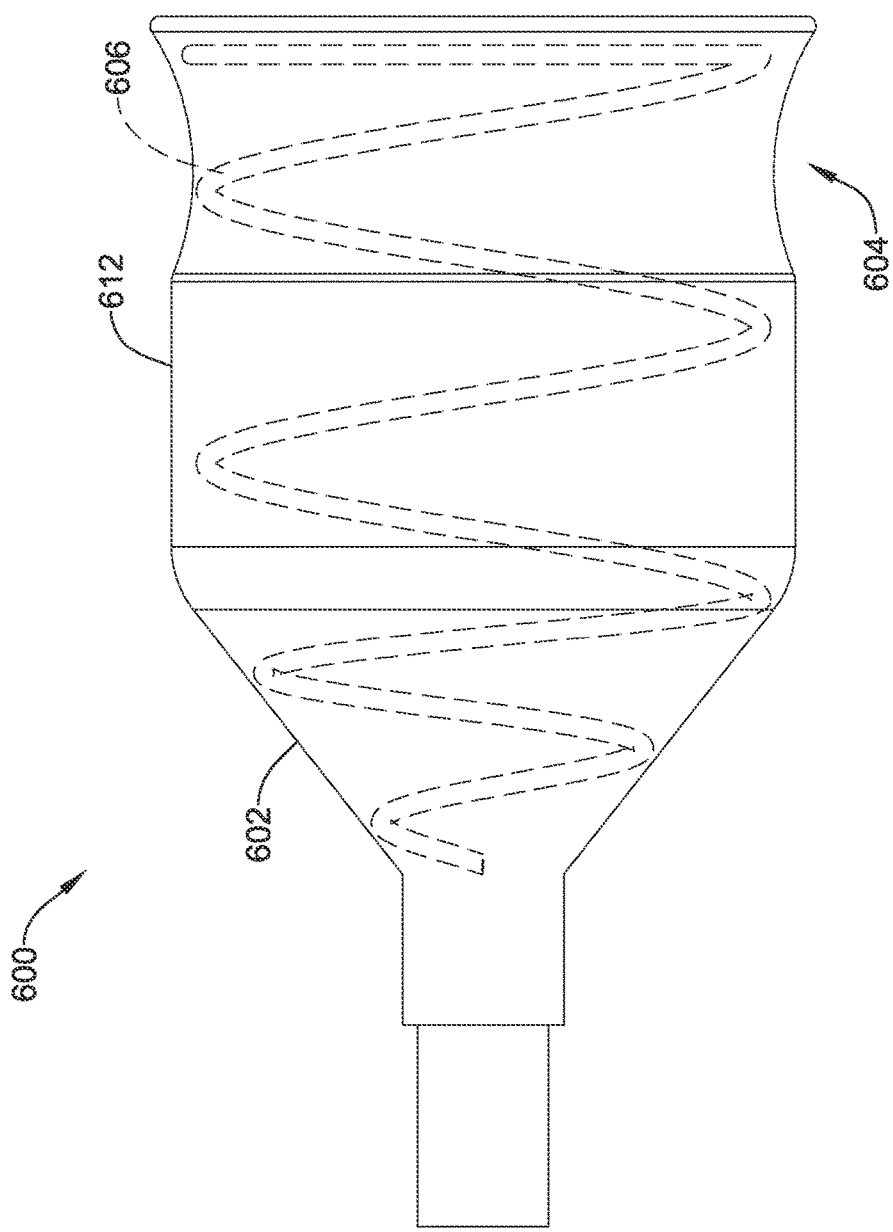

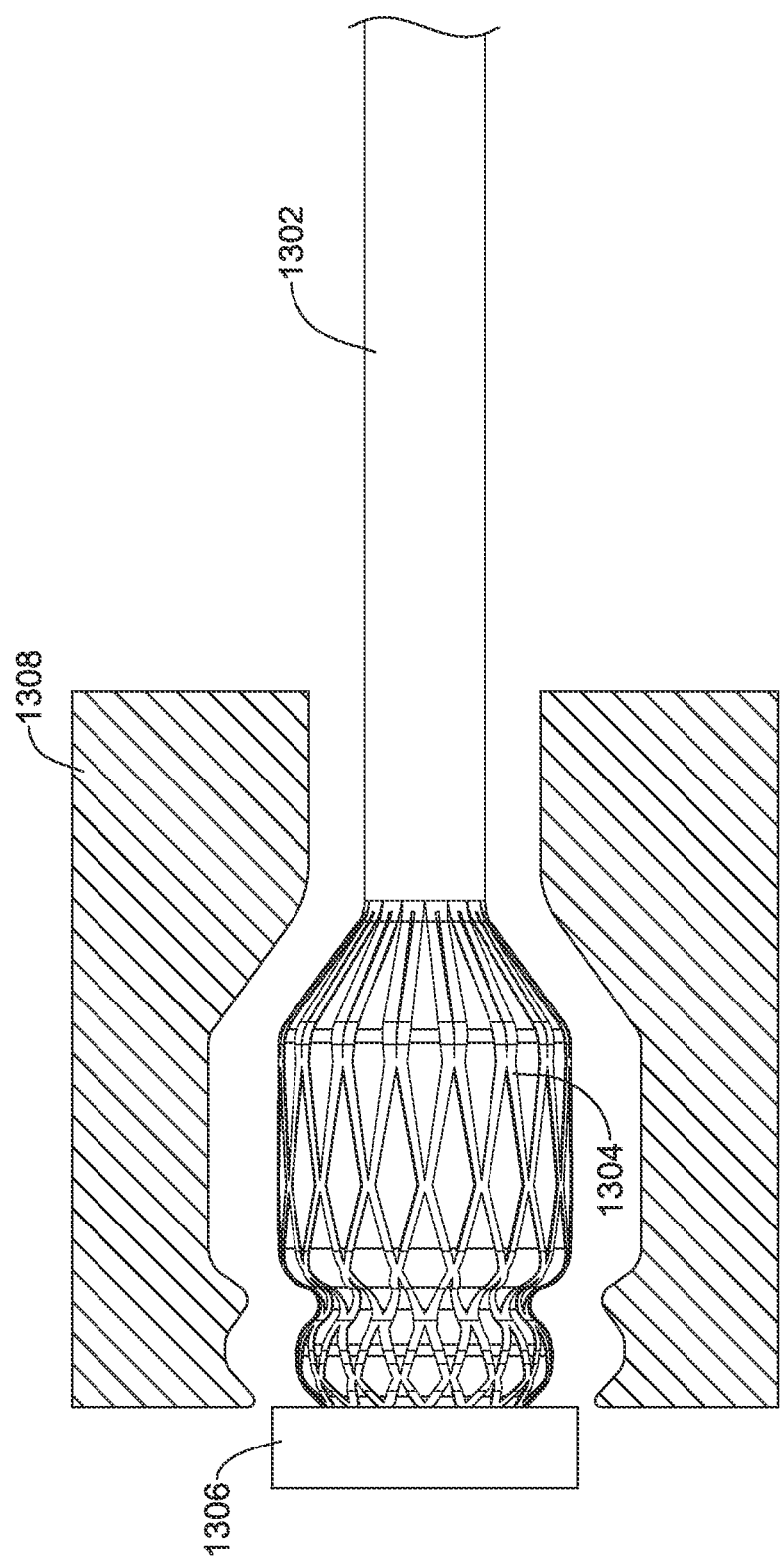

METHODS AND SYSTEMS FOR LOADING AND DELIVERING A STENT

CROSS-REFERENCE TO RELATED APPLICATIONS

This application claims priority to U.S. Provisional Application Ser. No. 61/890,999, filed Oct. 15, 2013, the entirety of which is incorporated herein by reference.

TECHNICAL FIELD

Some embodiments relate to medical devices for loading and delivering stents, and methods for manufacturing and using the same. More particularly, the present disclosure relates to methods and systems for loading a stent prior to deployment of the stent within a lumen of a human body.

BACKGROUND

The body includes various passageways including blood vessels, such as arteries, urinary, biliary, tracheobronchial, esophageal or renal tracts, etc. These passageways sometimes become occluded or weakened, or otherwise in need of structural support. For example, they can be occluded by a tumor, restricted by plaque, or weakened by an aneurysm. When this occurs, the passageway can be reopened or reinforced, or even replaced, with a medical endoprosthesis. The endoprosthesis may be implanted in a passageway or lumen in the body. Many endoprostheses are tubular members, examples of which include stents, stent grafts, covered stents, aortic valves, etc.

Some endoprosthesis devices, such as polymeric stent platforms, may be shipped to a customer in an expanded state. In these cases, a physician may be required to constrain the stent onto a stent delivery system prior to inserting the stent delivery system into the patient. Accordingly, it is desirable to provide alternative stent constrainment mechanisms to facilitate constraining the stent into the stent delivery system for use during a medical procedure.

SUMMARY

One illustrative embodiment includes a stent loading and delivery device. The stent loading and delivery device includes a handle assembly and an outer tubular member extending distally from the handle assembly. The outer tubular member has a proximal end and a distal end, the proximal end of the outer tubular member is attached to a first handle of the handle assembly. The device also includes an intermediate tubular member slidably disposed within the outer tubular member. The intermediate tubular member has a proximal end and a distal end. The proximal end of the intermediate tubular member is attached to a second handle of the handle assembly. The device also includes an inner elongate member extending distally from the handle assembly within the intermediate tubular member. The inner elongate member has a proximal end and a distal end, and the proximal end of the inner elongate member is attached to a third handle of the handle assembly. The device also includes a stent constrainment mechanism attached to the distal end of the intermediate tubular member. The stent constrainment mechanism can receive a proximal portion of a stent into a distal opening of the stent constrainment mechanism in an expanded state, and upon longitudinal actuation of the outer tubular member relative to the intermediate tubular member, the stent constrainment mechanism is configured to collapse radially inward around the stent to constrain the stent within the outer tubular member.

Another embodiment includes a stent loading and delivery device having a handle assembly and a first tubular member extending distally from the handle assembly to a distal end of the first tubular member. The stent loading and delivery device also includes a second tubular member disposed within the first tubular member. The second tubular member includes a proximal end and a distal end. The handle assembly can actuate the first tubular member relative to the second tubular member in a longitudinal direction between a first position and a second position. The delivery device further includes a stent constrainment mechanism attached to the distal end of the second tubular member. The stent constrainment mechanism can receive a proximal portion of a stent into a distal opening of the stent constrainment mechanism in an expanded state, wherein upon longitudinal actuation of the first tubular member relative to the second tubular member the stent constrainment mechanism is configured to collapse radially inward around the stent to constrain the stent within the first tubular member. The stent constrainment mechanism may include a conical portion extending distally from the distal end of the second tubular member. The conical portion expands in a distal direction from a first diameter at a proximal end of the conical portion located proximate the distal end of the second tubular member to a second diameter at a distal end of the conical portion. The stent constrainment mechanism also includes a necked portion located distal of the conical portion. The necked portion has a diameter less than the second diameter of the conical portion.

Yet another illustrative embodiment includes a method of loading a stent in a stent delivery device. The method includes inserting a proximal portion of a stent into a distal opening of the stent constrainment mechanism as disclosed above.

The above summary of some embodiments is not intended to describe each disclosed embodiment or every implementation of the present disclosure. The Figures, and Detailed Description, which follow, more particularly exemplify these embodiments, but are also intended as exemplary and not limiting.

BRIEF DESCRIPTION OF THE DRAWINGS

The disclosure may be more completely understood in consideration of the following detailed description of various embodiments in connection with the accompanying drawings, in which:

FIGS. 6A and 6B are perspective and side views, respectively, of an alternative stent constrainment mechanism for use with the stent loading and delivery system of FIG. 1;

FIGS. 13A, 13B and 13C illustrate aspects of forming a stent constrainment mechanism;

DETAILED DESCRIPTION

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings, in which similar elements in different drawings are identified with the same reference numbers. The drawings, which are not necessarily to scale, depict illustrative embodiments and are not intended to limit the scope of the disclosure.

Figure 1:
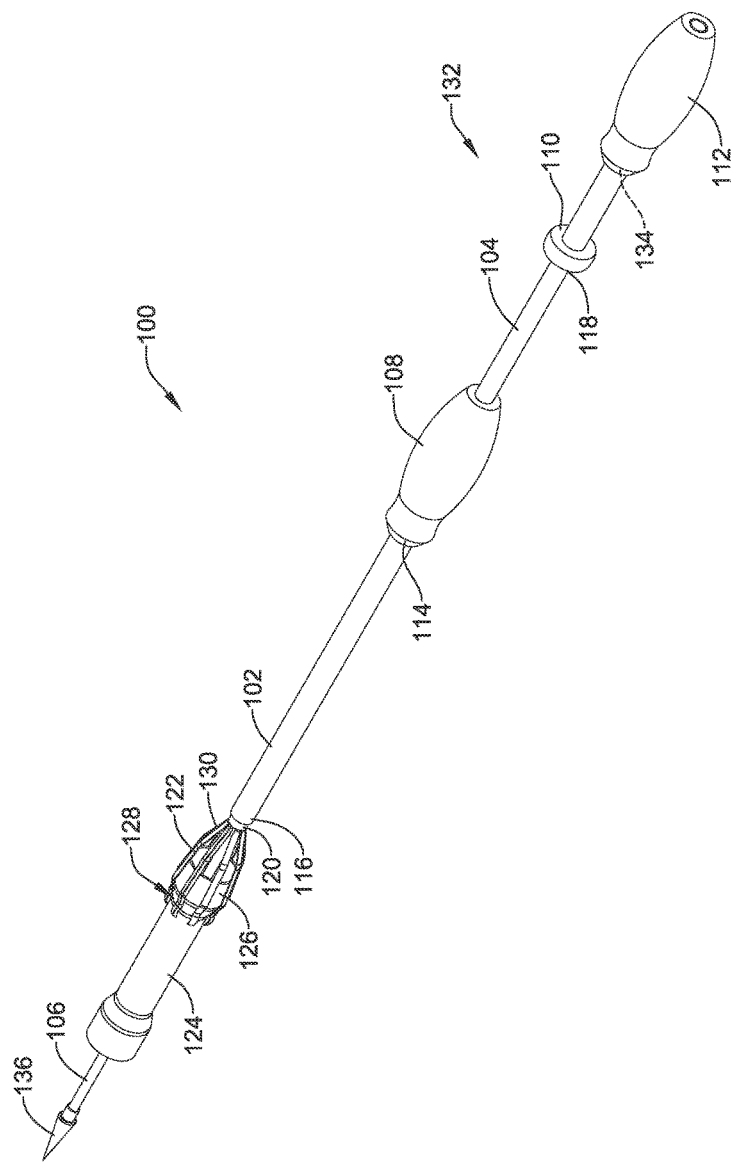
FIG. 1 is a perspective view of an exemplary stent loading and delivery system, in accordance with some embodiments of the present disclosure.

FIG. 1 is a perspective view of an exemplary stent loading and delivery system 100, in accordance with some embodiments of the present disclosure. The stent loading and delivery system 100 may include a handle assembly 132 having a first handle 108, a second handle 110, and a third handle 112. The handle assembly 132 may be located at a proximal end of the stent loading and delivery system 100. The stent loading and delivery system 100 also may include an outer tubular member 102 (or a first tubular member 102) extending distally from the handle assembly 132. The outer tubular member 102 includes a proximal end 114 and a distal end 116. The proximal end 114 may be attached to the first handle 108 of the handle assembly 132.

The stent loading and delivery device 100 may further include an intermediate tubular member 104 (or second tubular member 104) slidably disposed within the outer tubular member 102. The intermediate tubular member 104 also includes a proximal end 118 and a distal end 120. The proximal end 118 of the intermediate tubular member 104 may be attached to the second handle 110 of the handle assembly 132. The distal end 120 may be configured to engage a proximal portion 130 of a stent constraint mechanism 122. In some embodiments, the handle assembly 132 may be configured to actuate (or move) the outer tubular member 102 relative to the intermediate tubular member 104 in a longitudinal direction between a first position and a second position. For example, movement of the first handle 108 relative to the second handle 110 may longitudinally actuate the outer tubular member 102 proximally or distally relative to the intermediate tubular member 104.

The stent loading and delivery device 100 may also include an inner elongate member 106 extending distally from the handle assembly 132 within the intermediate tubular member 104. The inner elongate member 106 also includes a proximal end 134 and a distal end 136. In some instances, the inner elongate member 106 may be a tubular member having a lumen extending therethrough. In other instances, the inner elongate member 106 may be a solid shaft without a lumen. The proximal end 134 of the inner elongate member 106 may be attached to the third handle 112 of the handle assembly 132.

The stent loading and delivery device 100 may also include a stent constrainment mechanism 122 disposed at the distal end 120 of the intermediate tubular member 104. The stent constrainment mechanism 122 may be used to constrain a stent 124 and load the constrained stent 124 into the device 100 prior to deployment within a lumen of a human body. The stent constrainment mechanism 122 may be configured to transition from an expanded state to a collapsed state and vice versa. The stent constrainment mechanism 122 may be configured to receive a proximal portion 126 of the stent 124 into a distal opening 128 of the stent constrainment mechanism 122 when the stent constraint mechanism 122 is in an expanded state as shown in FIG. 1.

A physician can cause the stent constrainment mechanism 122 to collapse by moving the outer tubular member 102 in a distal direction relative to the stent constrainment mechanism 122 and the intermediate tubular member 104 (e.g., by moving the first handle 108 in a distal direction relative to the second handle 110 and the third handle 112. Distal movement of the outer tubular member 102 relative to the stent constrainment mechanism 122 (and thus the intermediate tubular member 104) causes the distal end 116 of the outer tubular member 102 to engage the stent constrainment mechanism 122 and exert a force on the stent constrainment mechanism 122 as the stent constrainment mechanism 122 is drawn into the lumen of the outer tubular member 102. Thus, the movement of the intermediate tubular member 104 in the proximal direction relative to the outer tubular member 102 and handle 108 may cause the stent constrainment mechanism 122 to collapse radially inward due to a constraining force that is applied by the distal end 116 of the outer tubular member 102 as the stent constrainment mechanism 122 is drawn into the interior of the outer tubular member 102. As shown in FIG. 1, the stent constrainment mechanism 122 may surround at least a proximal portion 126 of the stent 124 such that as the stent constrainment mechanism 122 is radially collapsed and drawn into the lumen of the outer tubular member 102, the stent constrainment mechanism 122 may also cause the stent 124 to collapse or otherwise be constrained so that the stent 124 may be drawn into the lumen of the outer tubular member 102 as the outer tubular member 102 is moved distally over the stent constrainment mechanism 122 and the stent 124. Once the stent 124 is fully constrained within the outer tubular member 102, the stent constrainment mechanism 122 can be retracted proximally relative to the outer tubular member 102 and the stent 124 until the stent constrainment mechanism 122 is separated from the stent 124 (e.g., until the distal end of the stent constrainment mechanism 122 is actuated proximal of the proximal end of the stent 124). For example, the intermediate tubular member 104, along with the stent constrainment mechanism 122, may be actuated proximally relative to the outer tubular member 102, the inner elongate member 106 and the stent 124, to actuate the stent constrainment mechanism 122 proximal of the stent 124.

Some exemplary structures of the strain constrainment mechanism 122 are described in detail, herein, with reference to subsequent figures. In some instances, the stent constrainment mechanism 122 may include a thin polymeric film and/or an expandable framework configured to surround and collapse over at least a proximal end portion of the stent 124. In some embodiments, the expandable framework may include a braided or woven structure, one or more struts, an expandable mesh, or other structure configured to collapse around the stent 124.

Figure 2:
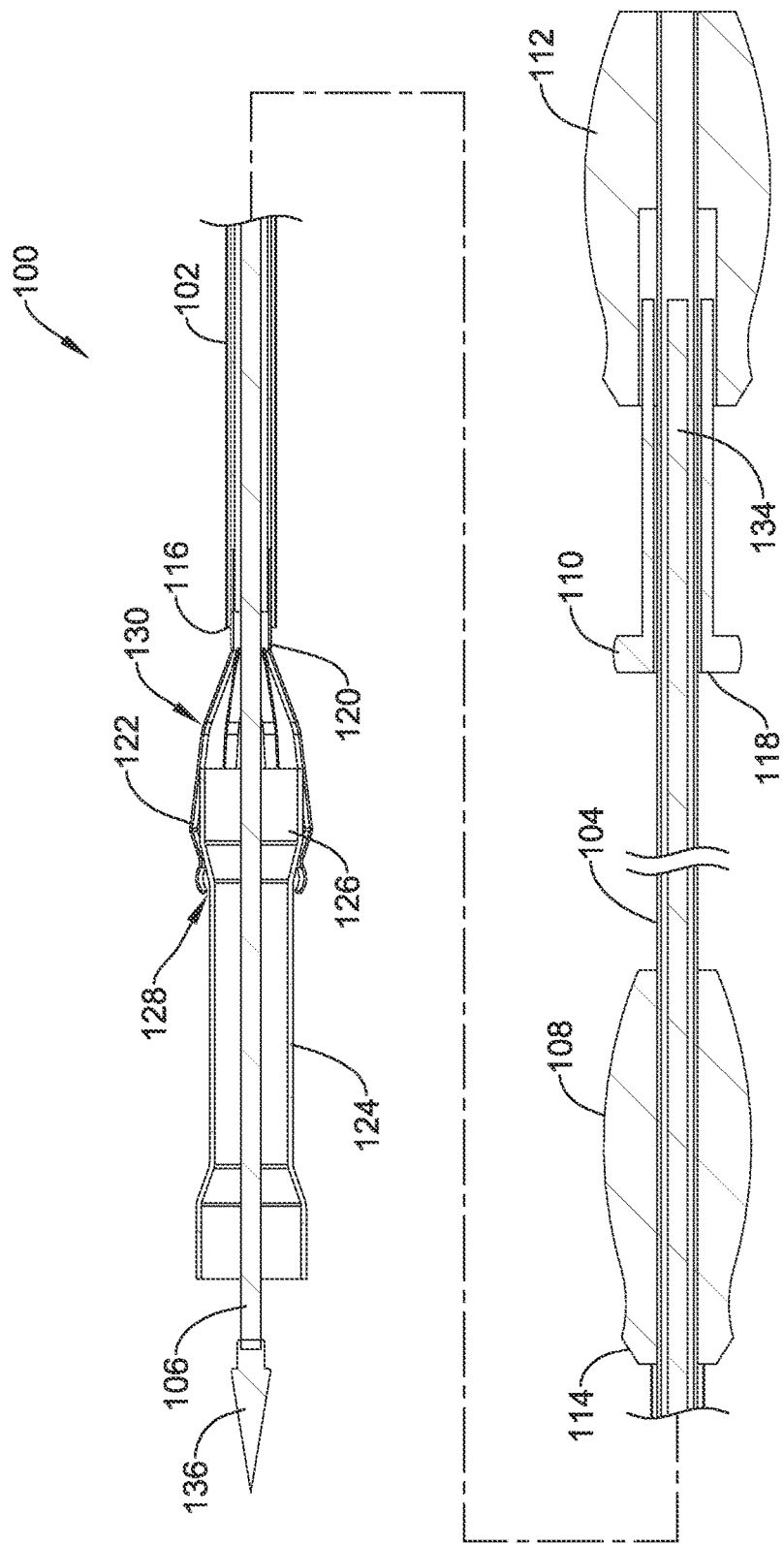
FIG. 2 is a longitudinal cross-sectional view of the exemplary stent loading and delivery system of FIG. 1.

FIG. 2 is a longitudinal cross-sectional view of the exemplary stent loading and delivery system 100 shown in FIG. 1. As discussed with reference to FIG. 1, the stent 124 can be loaded within the stent constrainment mechanism 122 prior to being loaded into the distal portion of the outer tubular member 102. In some embodiments, the proximal portion 126 of the stent 124 may be inserted into the distal opening 128 of the stent constrainment mechanism 122. The outer tubular member 102 can be actuated distally relative to the intermediate tubular member 104 by actuating the handle assembly 132, such as manipulating the first handle 108 relative to the second handle 110 of the handle assembly 132, or otherwise actuating the outer tubular member 102 relative to the intermediate tubular member 104 (e.g., actuating the outer tubular member 102 distally and/or actuating the intermediate tubular member 104 proximally).

The stent constrainment mechanism 122 may expand to a radially expanded state when the stent constrainment mechanism 122 is actuated distally of the outer tubular member 102, permitting the stent 124 to be loaded into the stent constrainment mechanism 122. In some instances, the stent constrainment mechanism 122 may be biased to the expanded state such that the stent constrainment mechanism 122 is configured to automatically radially expand to the expanded state when unconstrained by the outer tubular member 102. As the outer tubular member 102 is actuated or slid distally, the stent constraint mechanism 122 may radially collapse towards the longitudinal axis of the stent loading and delivery device 100 forcing the stent 124 to collapse to a reduced, contracted state within the outer tubular member 102. Once the stent 124 is fully constrained within the lumen of the outer tubular member 102, the stent constraining mechanism 122 can be retracted further proximally until the stent constraining mechanism 122 is positioned proximal of the stent 124 and fully separated from the stent 124. The delivery device 100 is then ready to be inserted into the patient's body, with the stent 124 constrained in the lumen of the outer tubular member 102 and released from the stent constrainment mechanism 122.

When the stent loading and delivery device 100 is at the desired location within the patient's body, the outer tubular member 102 can be retracted proximally relative to the stent 124 to expel the stent 124 out of the distal end of the outer tubular member 102 to allow the stent 124 to expand to a radially expanded state. The stent constraining mechanism 122 can remain constrained within the delivery device 100 as the stent 124 is deployed from the delivery device 100. In some instances, the stent constraining mechanism 122 can be made of thin metal using a suitable method, such as, progressive die stamping and rolling/forming, or made of a polymeric material by injection molding as a single or multiple components, for example. In other instances, the stent constrainment mechanism 122 may include an expandable framework formed of one or more filaments, such as a braided framework, a helical framework, or other construction. In some instances, the stent constrainment mechanism 122 may include a monolithic expandable framework, if desired.

In some embodiments, the stent constrainment mechanism 122 may include a tubular polymeric membrane configured to be expanded to the radially expanded state and contracted to the radially contracted state. In some instances, the tubular polymeric membrane may be molded to an expandable framework, such as molded to multiple circumferentially arranged members or one or more helical members, for example. In some embodiments, the tubular polymeric membrane may extend distally from the distal end 120 of the intermediate tubular member 104. Further, the stent constrainment mechanism 122 may include a number of circumferentially arranged members (e.g. 306 in FIG. 3A) that can extend distally from the distal end 120 of the intermediate tubular member 104. The stent constrainment mechanism 122 may be formed using any biocompatible polymers, metals, metal alloys, and combinations thereof.

The stent constrainment mechanism 122 may be attached to the distal end 120 of the intermediate tubular member 104 and extend distally therefrom. The stent constrainment mechanism 122 may include a distal opening into which the stent 124 may be positioned. The stent constrainment mechanism 122 may include a conical portion that may extend distally from the distal end 120 of the intermediate tubular member which may expand in a distal direction from a first diameter at a proximal end of the conical portion located proximate to the distal end 120 of the intermediate tubular member 104 to a second diameter at a distal end of the conical portion. The conical portion of the stent constrainment mechanism 122 may be configured to collapse as the distal end of the outer tubular member 102 is pressed against the conical portion, and likewise, the conical portion may be configured to expand when freed from the outer tubular member 102.

The stent constrainment mechanism 122 may also include a necked portion located distal of the conical portion. The necked portion may have a diameter less than a more distal portion of the stent constrainment mechanism 122 distal of the necked portion. For example, the necked portion may have a diameter less than the distal end region of the stent constrainment mechanism 122. In some embodiments, the necked portion may have a diameter less than the second diameter of the conical portion.

Various exemplary configurations of the stent constrainment mechanism 122 will be described in detail in the subsequent figures.

Figure 3A:
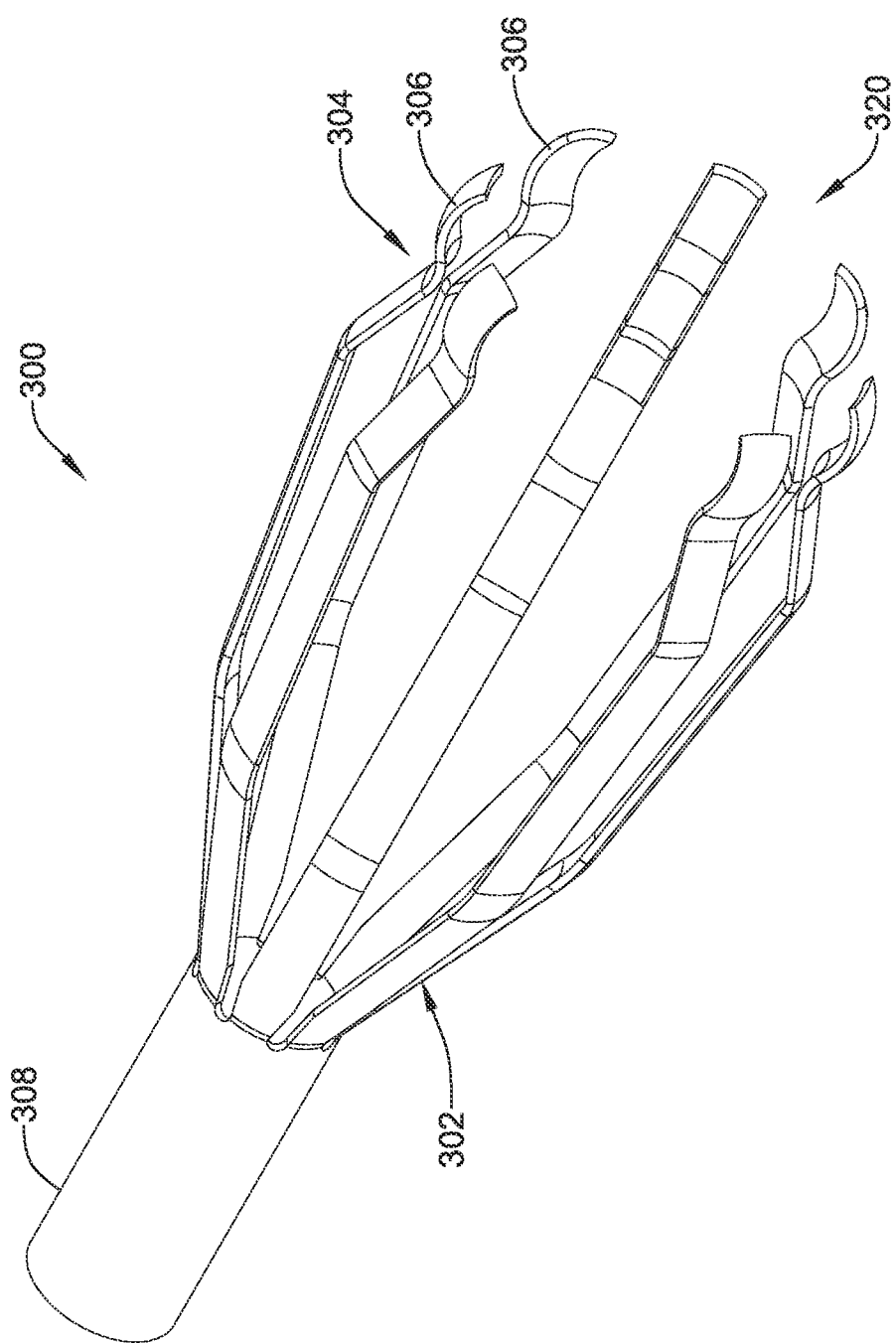
FIGS. 3A and 3B are perspective and side views, respectively, of an exemplary stent constrainment mechanism for use with the stent loading and delivery system of FIG. 1.
Figure 3B:
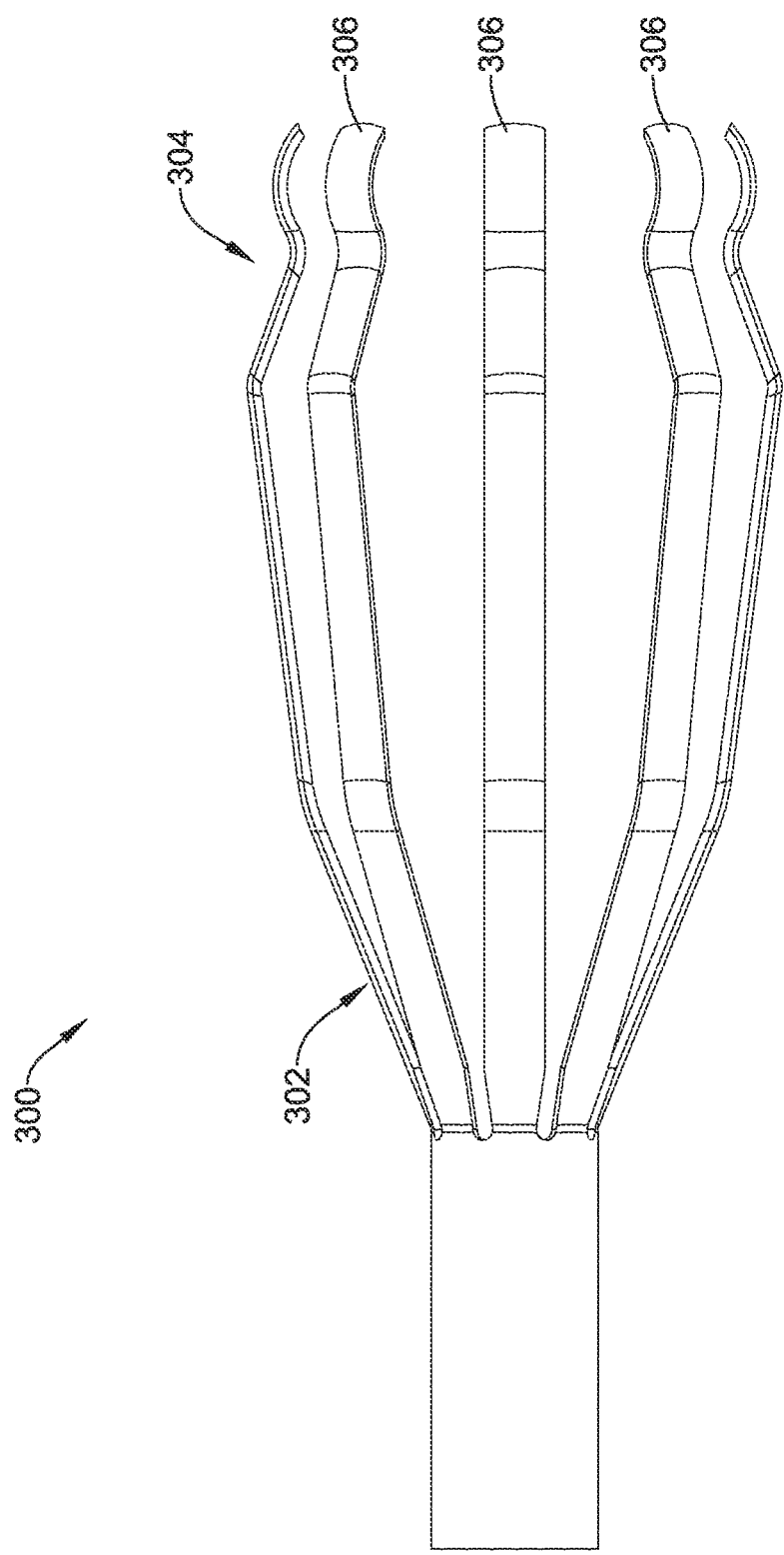

FIGS. 3A and 3B are perspective and side views, respectively, of an exemplary stent constrainment mechanism 300 for use with the stent loading and delivery system 100 of FIG. 1. The stent constrainment mechanism 300 may be attached to the distal end 120 of the intermediate tubular member 104 and extend distally therefrom. For example, the stent constrainment mechanism 300 may include a proximal tubular portion 308 configured to be positioned within or around the distal end portion of the intermediate tubular member 104 and attached thereto.

As shown, the stent constrainment mechanism 300 may include a conical portion 302 that may extend distally from the distal end 120 of the intermediate tubular member 104 shown in FIG. 1. The stent constrainment mechanism 300 may include a distal opening 320 into which the stent 124 may be positioned. Further, the conical portion 302 may expand in a distal direction from a first diameter at a proximal end of the conical portion 302 located proximate to the distal end 120 of the intermediate tubular member 104 to a second diameter at a distal end of the conical portion 302. The conical portion 302 of the stent constrainment mechanism 300 may be configured to collapse as the distal end of the outer tubular member 102 is pressed against the conical portion 302, and likewise, the conical portion 302 may be configured to expand when freed from the outer tubular member 102.

The stent constrainment mechanism 300 may also include a necked portion 304 located distal of the conical portion 302. The necked portion 304 may have a diameter less than a more distal portion of the stent constrainment mechanism 300 distal of the necked portion 304. For example, the necked portion 304 may have a diameter less than the distal end region of the stent constrainment mechanism 300. In some embodiments, the necked portion 304 may have a diameter less than the second diameter of the conical portion 302.

The stent constrainment mechanism 300 may include a plurality of circumferentially arranged members 306 (e.g., fingers, struts, etc.) extending distally from the tubular portion 308 in a longitudinal direction. In some embodiments, the circumferentially arranged members 306 may be finger like projections extending distally from the distal end 120 of the intermediate tubular member 104. Alternatively, the circumferentially arranged members 306 may be formed as a monolithic portion of the intermediate tubular member 104, or the circumferentially arranged members 306 may attach to an anchoring component (not shown) that may be directly adhered to or molded directly onto the intermediate tubular member 104 of the stent loading and delivery system 100. The number and/or arrangement of circumferentially arranged members 306 may be selected, as desired. For example, the stent constrainment mechanism 300 may include two, three, four, five, six, seven, eight, nine, ten, or more circumferentially arranged members 306 symmetrically or asymmetrically arranged around the circumference, as desired.

The circumferentially arranged members 306 may be formed using any desired material, such as a metallic material or a polymeric material. In some instances, the circumferentially arranged members 306 may be formed from a thin metal or polymeric sheet with different cut patterns formed therein and rolled into a tubular configuration. The cut patterns may vary depending on the desired shape and size stent constrainment mechanism 300. The cut patterns may facilitate radially compression/expansion (e.g., change in diameter) and/or elongation (e.g., change in length) of the stent constrainment mechanism 300. In some embodiments, the width, shape, and/or length of each of the circumferentially arranged members 306 may vary depending on the desired characteristics of the stent constrainment mechanism 300. For example, as shown in FIGS. 3A-3B, each of the circumferentially arranged members 306 may be a thin flat strip having a rectangular cross-section. But various other suitable cross-sections such as, but not limited to, circular, oval, and so forth are contemplated.

Figure 4A:
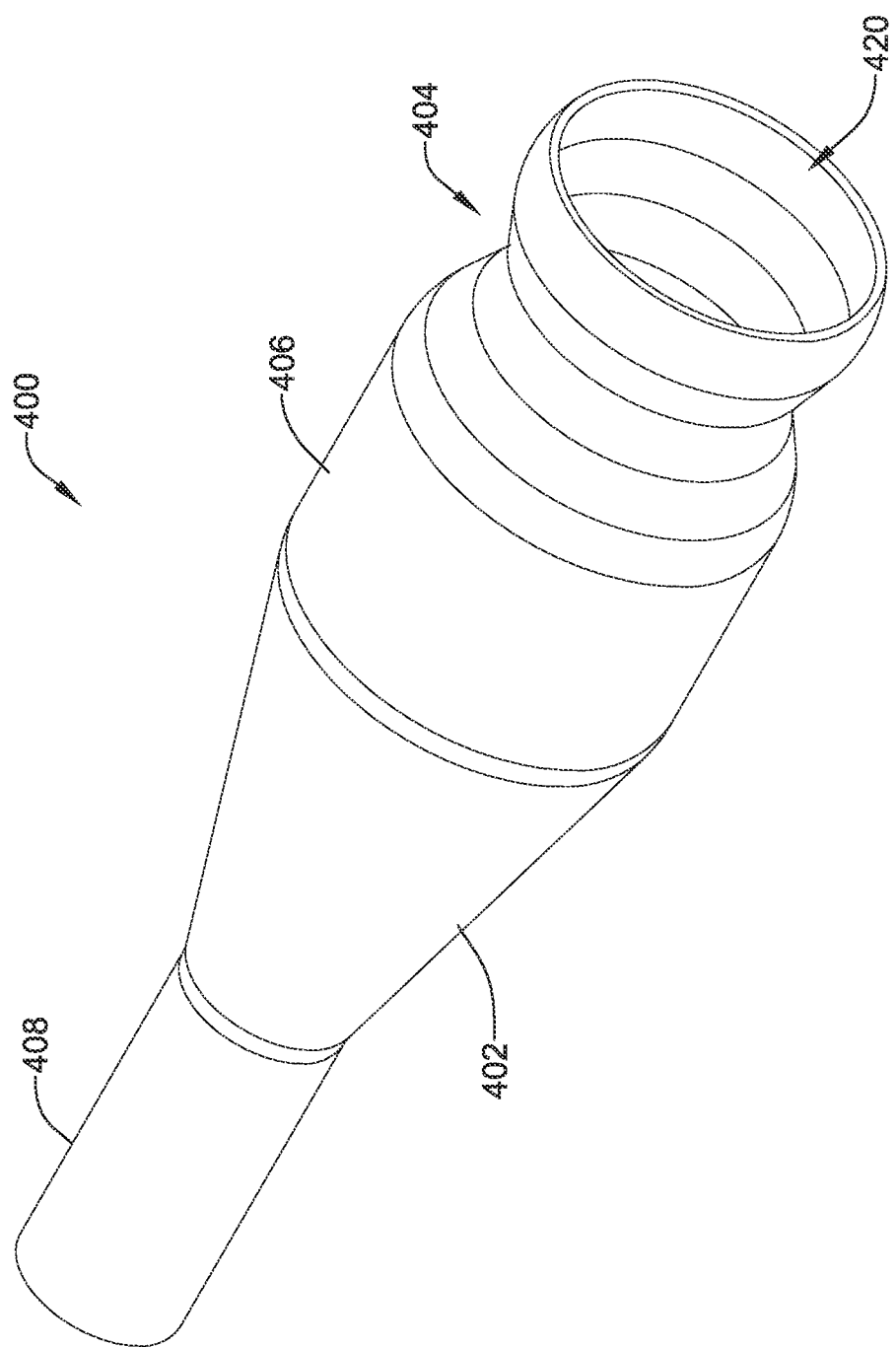
FIGS. 4A and 4B are perspective and side views, respectively, of an alternative stent constrainment mechanism for use with the stent loading and delivery system of FIG. 1.
Figure 4B:
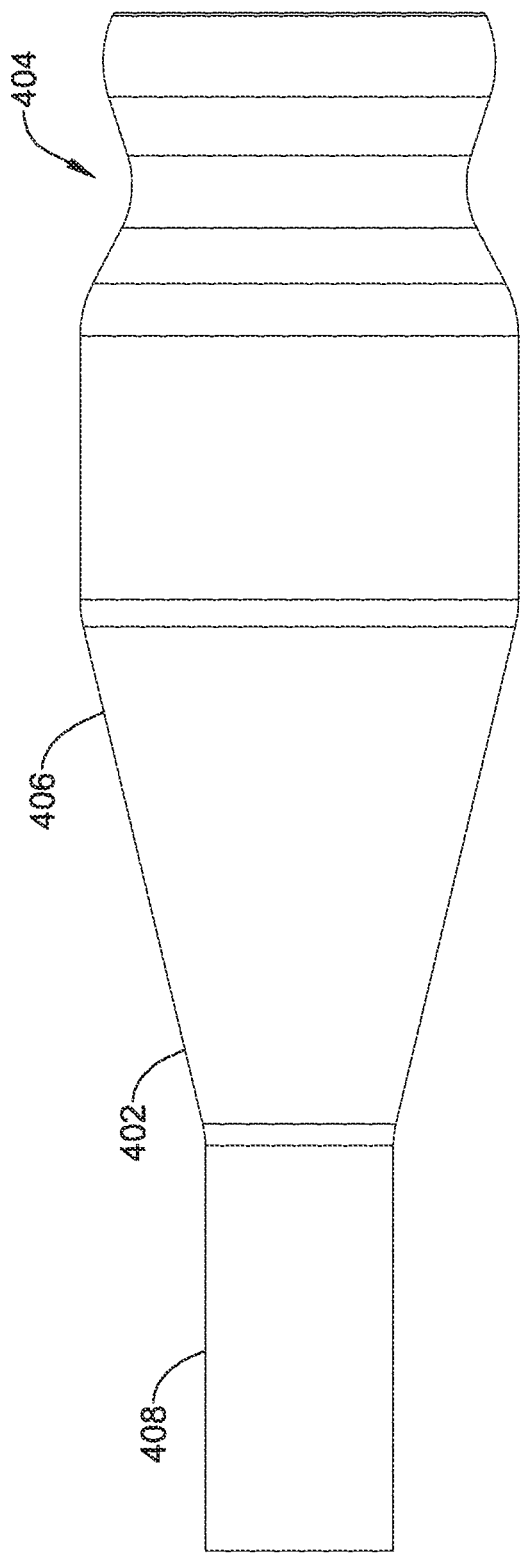

FIGS. 4A and 4B are perspective and side views, respectively, of an alternative stent constrainment mechanism 400 for use with the stent loading and delivery system 100 of FIG. 1. The stent constrainment mechanism 400 may be attached to the distal end 120 of the intermediate tubular member 104 and extend distally therefrom. For example, the stent constrainment mechanism 400 may include a proximal tubular portion 408 configured to be positioned within or around the distal end portion of the intermediate tubular member 104 and attached thereto. In alternative embodiments, the tubular polymeric membrane 406 may be a monolithic portion of the intermediate tubular member 104.

As shown, the stent constrainment mechanism 400 may include a tubular polymeric membrane 406 molded to a conical portion 402 and a necked portion 404 of the stent constrainment mechanism 400. The necked portion 404 may have a diameter less than a more distal portion of the stent constrainment mechanism 400 distal of the necked portion 404. For example, the necked portion 404 may have a diameter less than the distal end region of the stent constrainment mechanism 400. In some embodiments, the necked portion 404 may have a diameter less than the second diameter of the conical portion 402. The stent constrainment mechanism 400 may include a distal opening 420 into which the stent 124 may be positioned.

The stent constrainment mechanism 400 may be formed as a continuous tube like structure. The stent constrainment mechanism 400 may be formed using any biocompatible polymer, such as polyurethane, polyamide, silicone, or other desired polymeric material. The stent constrainment mechanism 400 may be formed using any suitable method, such as, but not limited to, overmolding, injection molding, dip molding, and so forth.

In some instances, the stent constrainment mechanism 400 may include a number of ribs or ridges (not shown) for providing strength. For example, the stent constrainment mechanism 400 may include a plurality of ribs or ridges extending longitudinally, circumferentially and/or helically along the polymeric membrane 406. For example, the ribs or ridges may be formed as a monolithic portion of the polymeric membrane 406 formed while forming the membrane 406. Alternatively, the ribs or ridges may be formed of fibers or strands of a different material embedded in the polymeric membrane 406. The stent constrainment mechanism 400 may also include pattern of cutouts for flexibility, if desired.

Figure 5A:
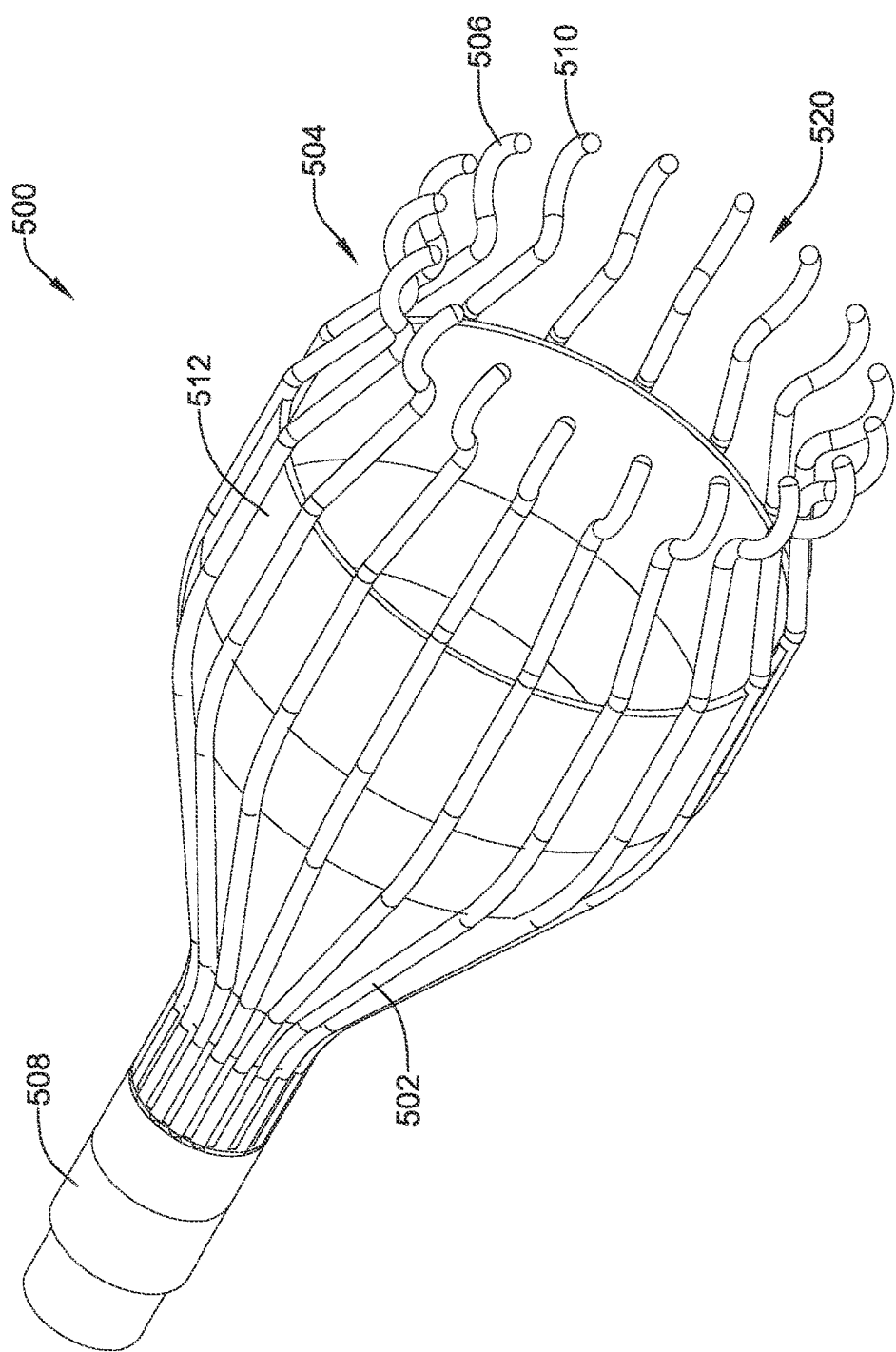
FIGS. 5A and 5B are perspective and side views, respectively, of an alternative stent constrainment mechanism for use with the stent loading and delivery system of FIG. 1.
Figure 5B:
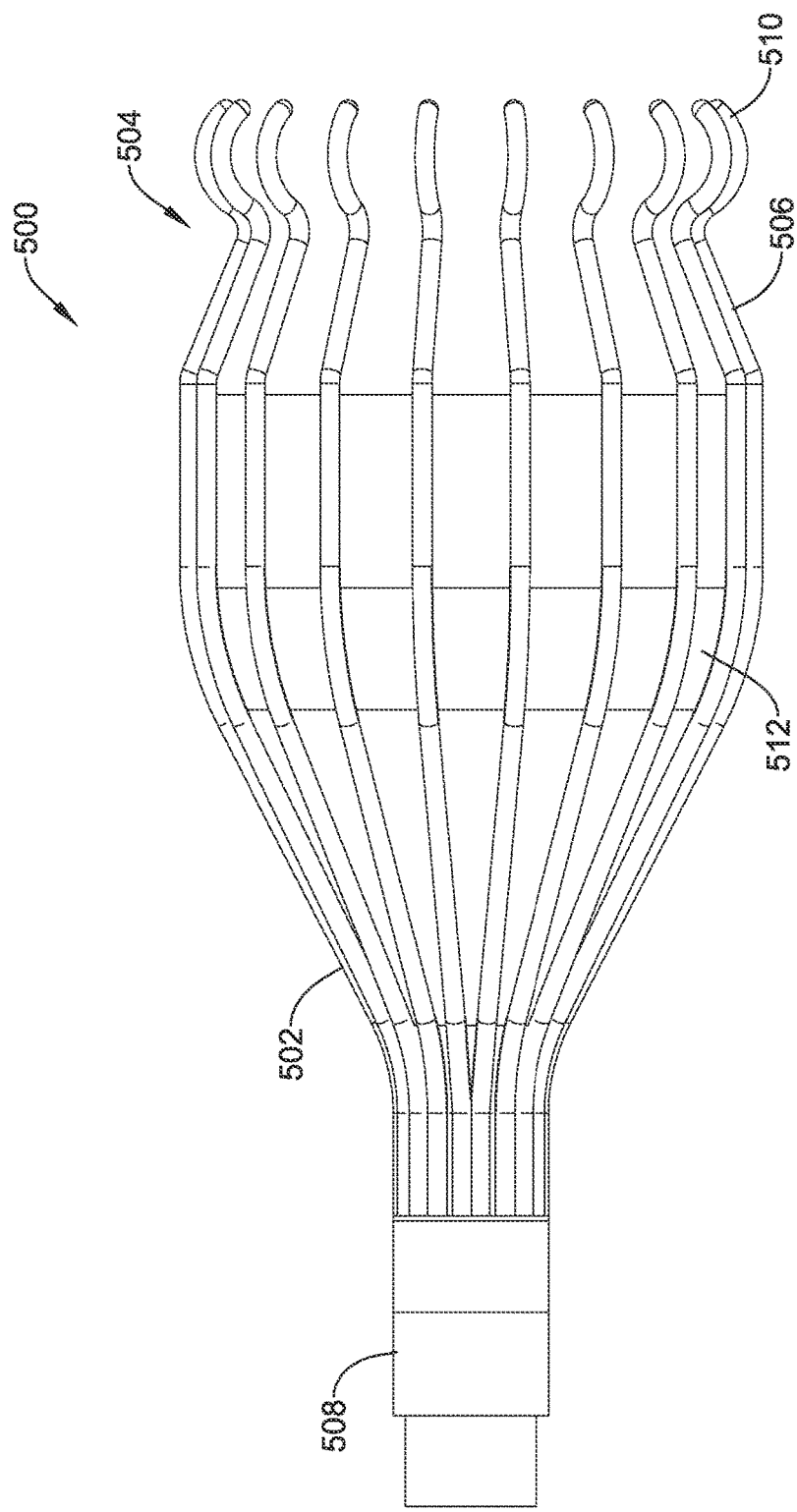

FIGS. 5A and 5B are perspective and side views, respectively, of an alternative stent constrainment mechanism 500 for use with the stent loading and delivery system 100. The stent constrainment mechanism 500 may be attached to the distal end 120 of the intermediate tubular member 104 and extend distally therefrom. For example, the stent constrainment mechanism 500 may include a proximal tubular portion 508 configured to be positioned within or around the distal end portion of the intermediate tubular member 104 and attached thereto.

The stent constrainment mechanism 500 may have a shuttle cock design including a number of circumferential arranged members 506 having a conical portion 502, and a necked portion 504 located distal of the conical portion 502. The stent constrainment mechanism 500 may include a distal opening 520 into which the stent 124 may be positioned. In some embodiments, the conical portion 502 may extend distally from the distal end 120 of the intermediate tubular member 104. Further, the conical portion 502 may expand in a distal direction from a first diameter at a proximal end of the conical portion 502 located proximate to the distal end 120 of the intermediate tubular member 104 to a second diameter at a distal end of the conical portion 502. The conical portion 502 of the stent constrainment mechanism 500 may be configured to collapse as the distal end of the outer tubular member 102 is pressed against the conical portion 502, and likewise, the conical portion 502 may be configured to expand when freed from the outer tubular member 102.

The necked portion 504 may have a diameter less than a more distal portion of the stent constrainment mechanism 500 distal of the necked portion 504. For example, the necked portion 504 may have a diameter less than the distal end region of the stent constrainment mechanism 500. In some embodiments, the necked portion 504 may have a diameter less than the second diameter of the conical portion 502.

The shape and size of the circumferentially arranged members 506 (e.g., fingers, struts, etc.) may vary, as desired. In some embodiments, the circumferentially arranged members 506 may be finger like projections extending distally from the distal end 120 of the intermediate tubular member 104. Further, each of the circumferentially arranged members 506 may have any suitable cross-section, such as, but not limited to, rectangular, oval, star-shaped, irregular, and so forth. In some embodiments, the circumferentially arranged members 506 may be attached to an anchoring component (not shown) that may be directly adhered to or molded directly onto the intermediate tubular member 104 of the stent loading and delivery system 100. The number of circumferentially arranged members 506 may be selected, as desired. For example, the stent constrainment mechanism 500 may include two, three, four, five, six, seven, eight, nine, ten, or more circumferentially arranged members 506 symmetrically or asymmetrically arranged around the circumference, as desired. The circumferential arranged members 506 may be curved distal of the necked portion 504 towards a distal end 510 of the circumferential arranged members 506.

The stent constrainment mechanism 500 may also include a thin film or a tubular polymeric membrane 512 molded to (e.g., over and/or under) the circumferentially arranged members 506. In some embodiments, the tubular polymeric membrane 512 may extend distally from the distal end 120 of the intermediate tubular member 104. In some instances, the tubular polymeric membrane 512 may include one or more cuts formed in the tubular polymeric membrane 512. The cut patterns may facilitate radial compression/expansion (e.g., change in diameter) and/or elongation (e.g., change in length) of the stent constrainment mechanism 500. The tubular polymeric membrane 512 may provide additional stability to the structure of the stent constrainment mechanism 500. Also, the tubular polymeric membrane 512 may be made up of a suitable flexible and/or elastic material that enables the stent constrainment mechanism 500 to retain its shape whether it is expanded or contracted. In some instances, the tubular polymeric membrane 512 may be molded onto the members 506, or the tubular polymeric membrane 512 may be formed separately and subsequently attached to the circumferentially arranged members 506 using a suitable method such as, but not limited to, adhesive bonding, thermal bonding, pressure bonding, or other desired attachment method.

In some instance, the stent constrainment mechanism 500 may further include a lubricious coating, such as a Teflon coating to reduce friction with the stent 124. The lubricious coating may be to an inner and/or outer surface of the stent constrainment mechanism 500.

FIGS. 6A and 6B are perspective and side views, respectively, of an alternative stent constrainment mechanism 600 for use with the stent loading and delivery system 100 of FIG. 1. The stent constrainment mechanism 600 may be attached to the distal end 120 of the intermediate tubular member 104 and extend distally therefrom. For example, the stent constrainment mechanism 600 may include a proximal tubular portion 608 configured to be positioned within or around the distal end portion of the intermediate tubular member 104 and attached thereto. The stent constrainment mechanism 600 may include a distal opening 620 into which the stent 124 may be positioned.

As shown, the stent constrainment mechanism 600 may include a conical portion 602 that may extend distally from the distal end 120 of the intermediate tubular member 104 shown in FIG. 1. Further, the conical portion 602 may expand in a distal direction from a first diameter at a proximal end of the conical portion 602 located proximate to the distal end 120 of the intermediate tubular member 104 to a second diameter at a distal end of the conical portion 602. The conical portion 602 of the stent constrainment mechanism 600 may be configured to collapse as the distal end of the outer tubular member 102 is pressed against the conical portion 602, and likewise, the conical portion 602 may be configured to expand when freed from the outer tubular member 102.

The stent constrainment mechanism 600 may also include a necked portion 604 located distal of the conical portion 602. The necked portion 604 may have a diameter less than a more distal portion of the stent constrainment mechanism 600 distal of the necked portion 604. For example, the necked portion 604 may have a diameter less than the distal end region of the stent constrainment mechanism 600. In some embodiments, the necked portion 604 may have a diameter less than the second diameter of the conical portion 602.

As shown, the stent constrainment mechanism 600 may have a funnel shaped design including one or more helical filaments 606 extending distally from the distal end 120 of the intermediate tubular member 104. The helical filaments 606 may be made up of suitable material such as, a metallic material (e.g., nitinol, stainless steel, titanium, etc.) or a polymeric material, as desired. In some instances, the helical filaments 606 may be a monofilament. In some embodiments, the helical filaments 606 can include multiple filaments joined together.

The stent constrainment mechanism 600 may also include a tubular polymeric membrane 612 molded to or otherwise attached to the one or more helical filaments 606. Similar to the polymer membrane 512, discussed above, the tubular polymeric membrane 612 may be attached to the helical filament(s) 606 in any desired fashion, such as molded onto the helical filament(s) 606 or otherwise bonded to the helical filament(s) 606. The material of the tubular polymeric membrane 612 may be formed of polyurethane, polyamide, silicone, and other biocompatible flexible material.

Figure 7A:
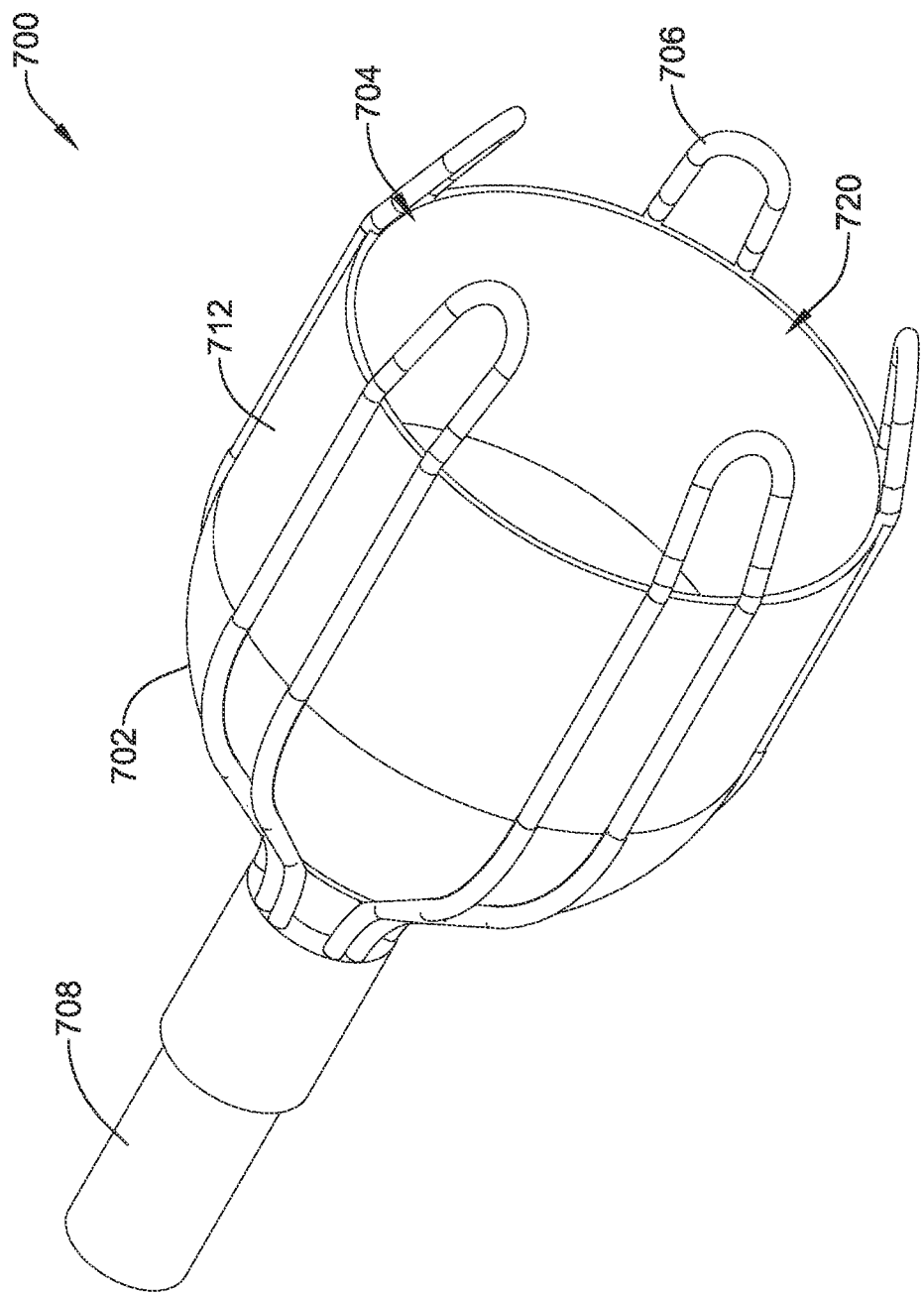
FIGS. 7A and 7B are perspective and side views, respectively, of an alternative stent constrainment mechanism for use with the stent loading and delivery system of FIG. 1.
Figure 7B:
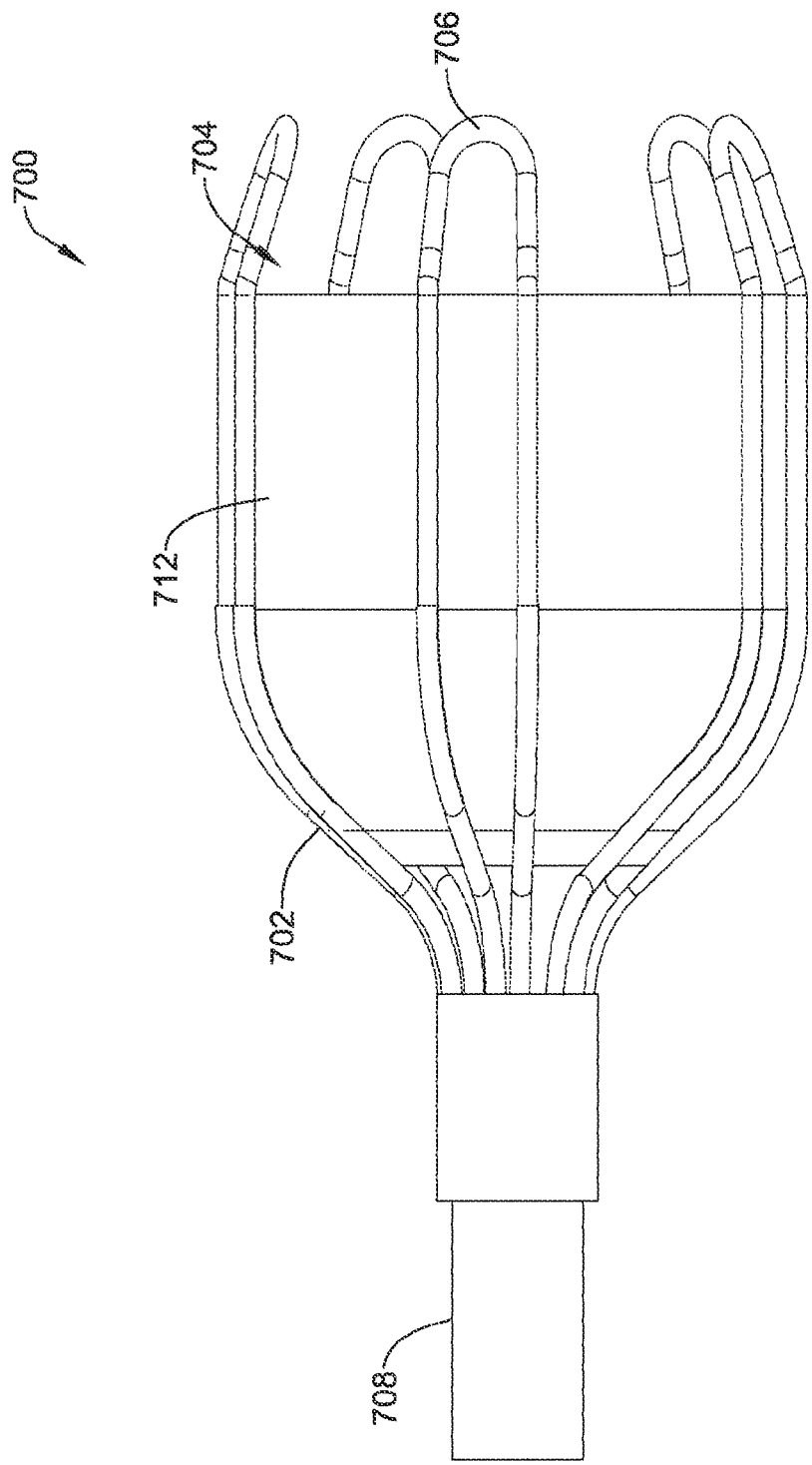

FIGS. 7A and 7B are perspective and side views, respectively, of an alternative stent constrainment mechanism 700 for use with the stent loading and delivery system 100 of FIG. 1. The stent constrainment mechanism 700 may be attached to the distal end 120 of the intermediate tubular member 104 and extend distally therefrom. For example, the stent constrainment mechanism 700 may include a proximal tubular portion 708 configured to be positioned within or around the distal end portion of the intermediate tubular member 104 and attached thereto. The stent constrainment mechanism 700 may include a distal opening 720 into which the stent 124 may be positioned.

As shown, the stent constrainment mechanism 700 may include a conical portion 702 that may extend distally from the distal end 120 of the intermediate tubular member 104 shown in FIG. 1. Further, the conical portion 702 may expand in a distal direction from a first diameter at a proximal end of the conical portion 702 located proximate to the distal end 120 of the intermediate tubular member 104 to a second diameter at a distal end of the conical portion 702. The conical portion 702 of the stent constrainment mechanism 700 may be configured to collapse as the distal end of the outer tubular member 102 is pressed against the conical portion 702, and likewise, the conical portion 702 may be configured to expand when freed from the outer tubular member 102.

The stent constrainment mechanism 700 may also include a necked portion 704 located distal of the conical portion 702. The necked portion 704 may have a diameter less than a more distal portion of the stent constrainment mechanism 700 distal of the necked portion 704. For example, the necked portion 704 may have a diameter less than the distal end region of the stent constrainment mechanism 700. In some embodiments, the necked portion 704 may have a diameter less than the second diameter of the conical portion 702.

The stent constrainment mechanism 700 may have a grasper design including a number of longitudinally extending ribs 706 or members that can strengthen the stent constrainment mechanism 700. The ribs 706 may be formed using suitable biocompatible metal, polymer, alloy or so forth. In some instances, each of the ribs 706 may form a looped distal portion with proximal portion extending proximally therefrom. The looped distal portion may be bent or angled radially inward while the proximal portions of the ribs 706 may extend generally parallel to the longitudinal axis of the stent constrainment mechanism 700, for example. The bent looped portion of the ribs 706 may form the necked portion 704 of the stent constrainment mechanism 700 in some instances.

The stent constrainment mechanism 700 may also include a tubular polymeric membrane 712 molded to or otherwise attached to the ribs 706. Similar to the polymer membrane 512, discussed above, the tubular polymeric membrane 712 may be attached to the ribs 706 in any desired fashion, such as molded onto the ribs 706 or otherwise bonded to the ribs 706. The material of the tubular polymeric membrane 712 may be formed of polyurethane, polyamide, silicone, and other biocompatible flexible material. In some instances, the polymeric membrane 712 may extend across or cover the proximal portions of the ribs 706 while the looped distal portions of the ribs 706 may not be covered by the polymeric membrane 712.

Figure 8A:
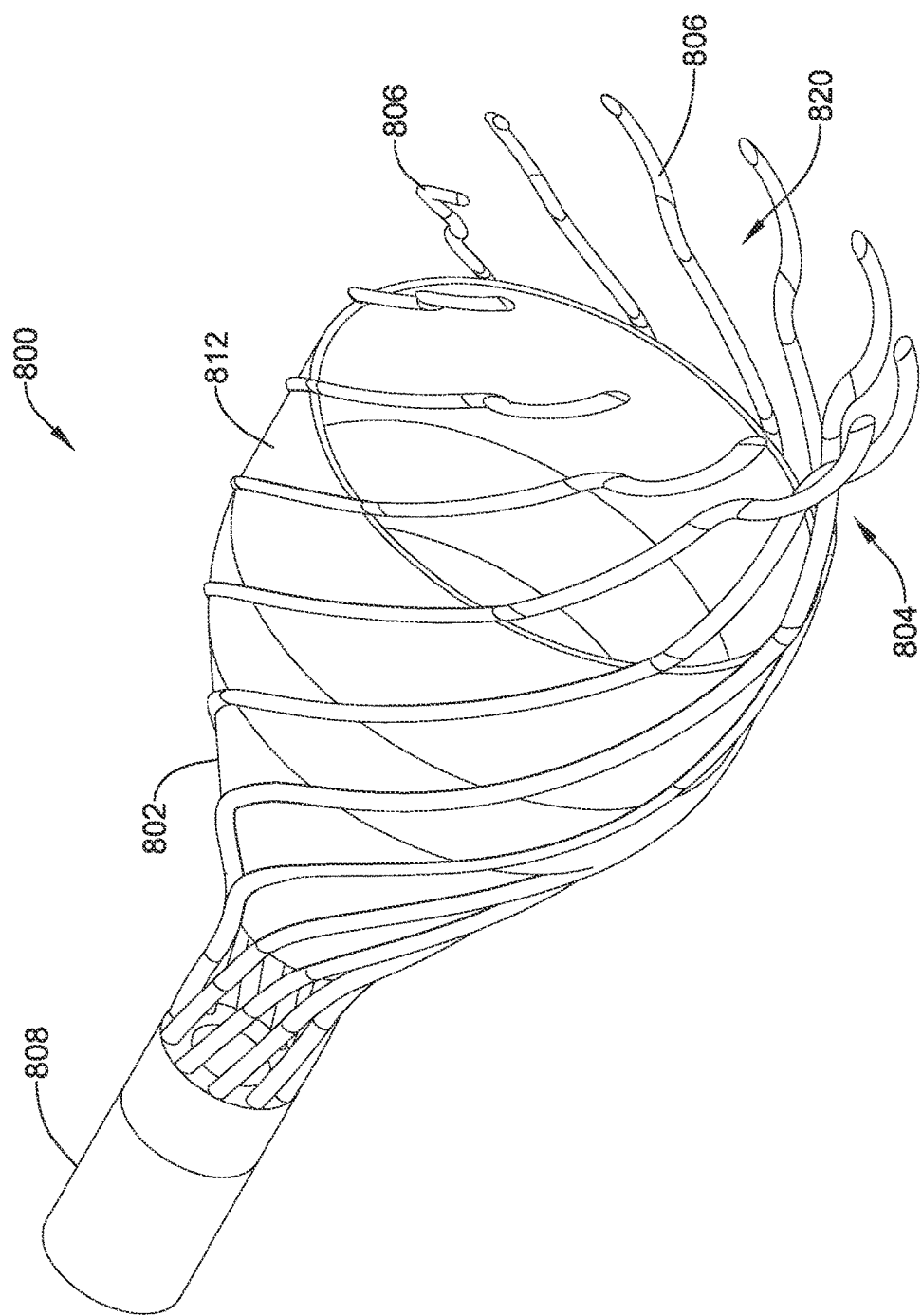
FIGS. 8A and 8B are perspective and side views, respectively, of an alternative stent constrainment mechanism for use with the stent loading and delivery system of FIG. 1.
Figure 8B:
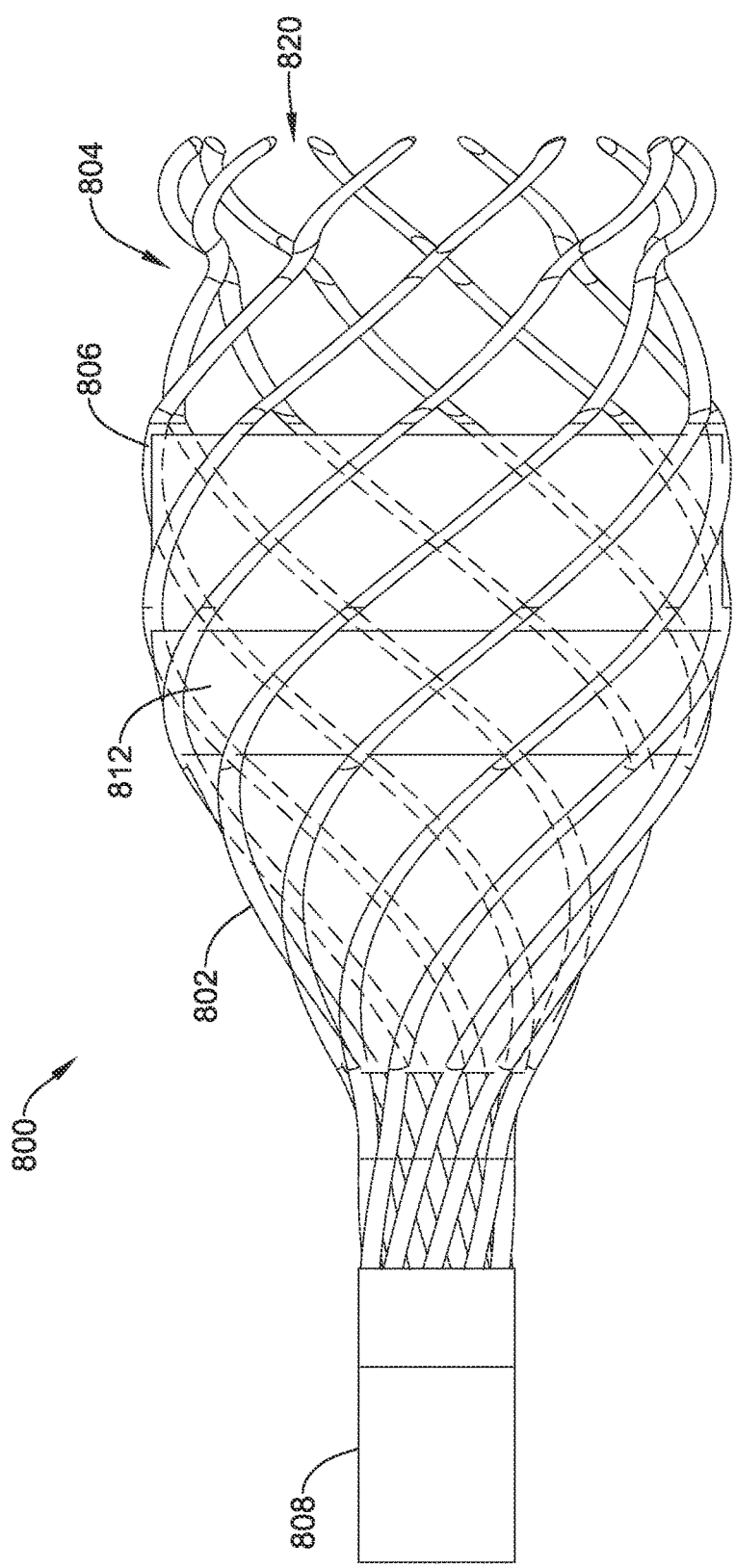

FIGS. 8A and 8B are perspective and side views, respectively, of an alternative stent constrainment mechanism 800 for use with the stent loading and delivery system 100 of FIG. 1. The stent constrainment mechanism 800 may be attached to the distal end 120 of the intermediate tubular member 104 and extend distally therefrom. For example, the stent constrainment mechanism 800 may include a proximal tubular portion 808 configured to be positioned within or around the distal end portion of the intermediate tubular member 104 and attached thereto. The stent constrainment mechanism 800 may include a distal opening 820 into which the stent 124 may be positioned.

As shown, the stent constrainment mechanism 800 may include a conical portion 802 that may extend distally from the distal end 120 of the intermediate tubular member 104 shown in FIG. 1. Further, the conical portion 802 may expand in a distal direction from a first diameter at a proximal end of the conical portion 802 located proximate to the distal end 120 of the intermediate tubular member 104 to a second diameter at a distal end of the conical portion 802. The conical portion 802 of the stent constrainment mechanism 800 may be configured to collapse as the distal end of the outer tubular member 102 is pressed against the conical portion 802, and likewise, the conical portion 802 may be configured to expand when freed from the outer tubular member 102.

The stent constrainment mechanism 800 may also include a necked portion 804 located distal of the conical portion 802. The necked portion 804 may have a diameter less than a more distal portion of the stent constrainment mechanism 800 distal of the necked portion 804. For example, the necked portion 804 may have a diameter less than the distal end region of the stent constrainment mechanism 800. In some embodiments, the necked portion 804 may have a diameter less than the second diameter of the conical portion 802.

The strain constrainment mechanism 800 have a multi start helical design including one or more helically arranged members 806 extending helically from the distal end 120 of the intermediate tubular member 104. In some embodiments, the helically arranged members 806 may be in form of helically arranged prongs or struts formed of a metallic or polymeric material, for example. In other instances, the helically arranged members 806 of the stent constrainment mechanism 800 may be cut from a metal or polymeric tube, for example.

The stent constrainment mechanism 800 may also include a polymeric membrane 812 molded to or otherwise attached to the helically arranged members 806. Similar to the polymer membrane 512, discussed above, the tubular polymeric membrane 812 may be attached to the helical members 806 in any desired fashion, such as molded onto the helical members 806 or otherwise bonded to the helical members 806. The material of the tubular polymeric membrane 812 may be formed of polyurethane, polyamide, silicone, and other biocompatible flexible material. In some instances, the polymeric membrane 812 may extend across or cover the proximal portions of the helical members 806 while the distal end portions of the helical members 806 may not be covered by the polymeric membrane 812.

Further as shown, each of the helically arranged members 806 has a circular cross section. However, in other instances any suitable cross-section such as, but not limited to, rectangular, oval, and so forth can be contemplated.

Figure 9A:
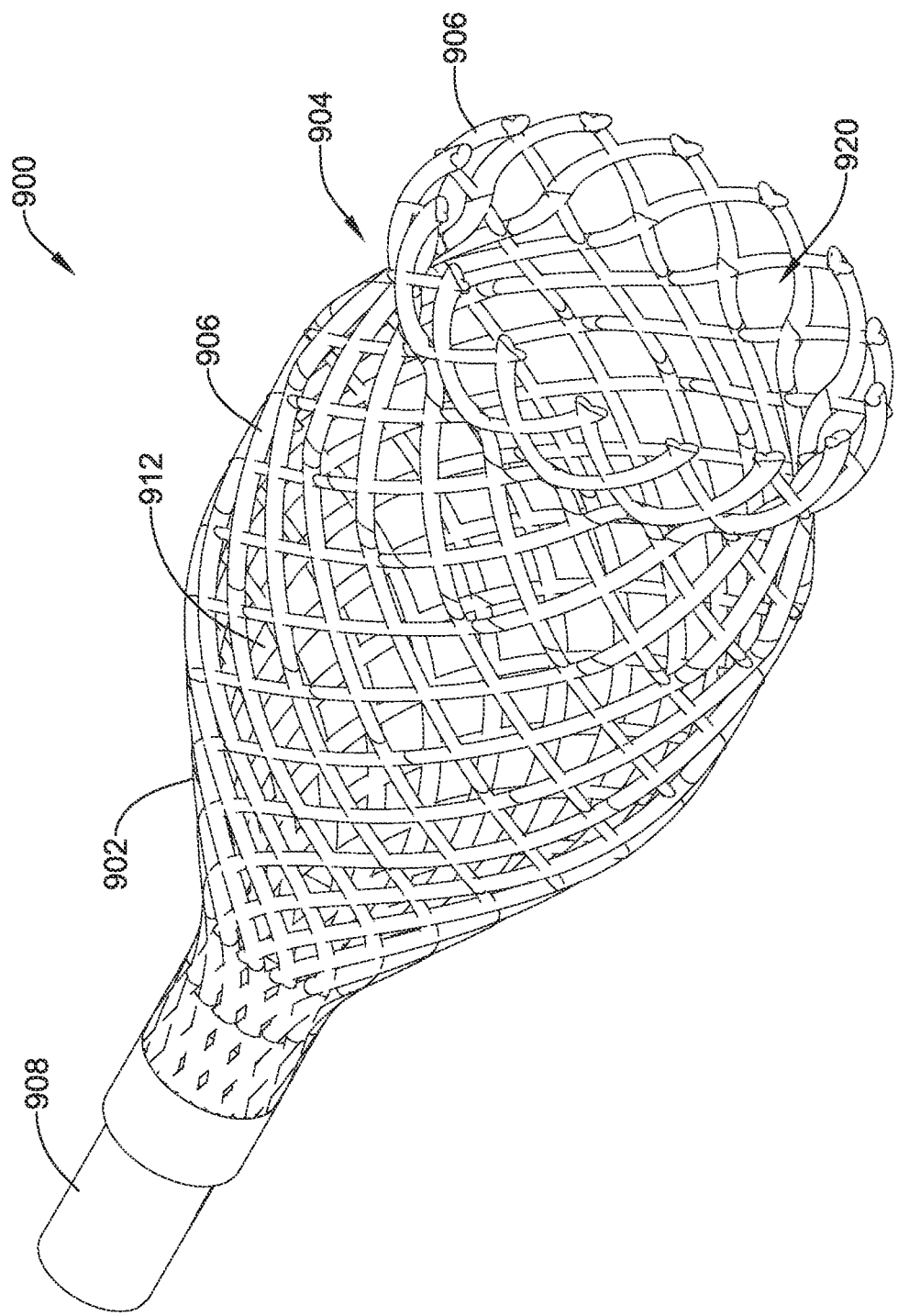
FIGS. 9A and 9B are perspective and side views, respectively, of an alternative stent constrainment mechanism for use with the stent loading and delivery system of FIG. 1.
Figure 9B:
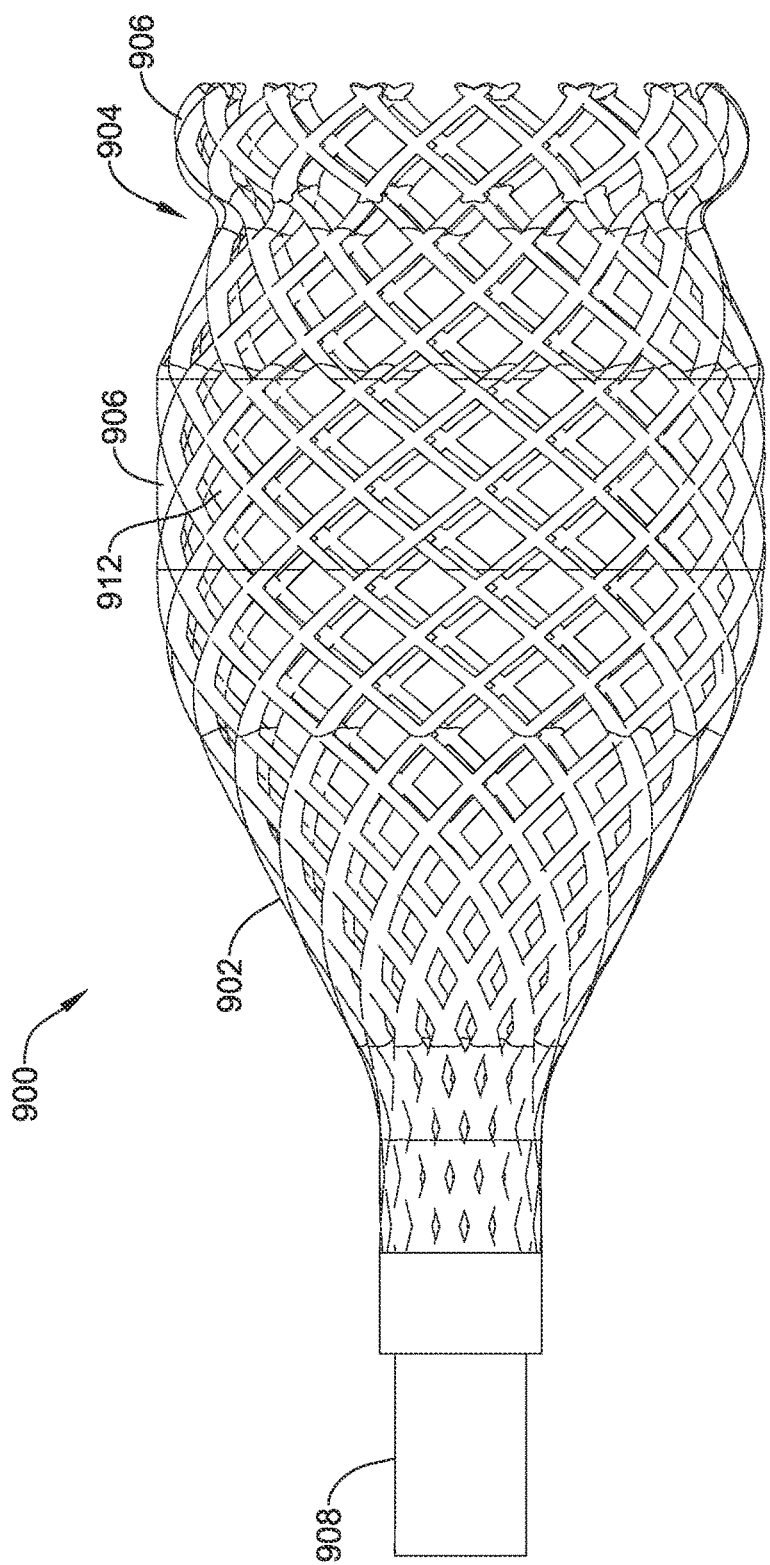

FIGS. 9A and 9B are perspective and side views, respectively, of an alternative stent constrainment mechanism 900 for use with the stent loading and delivery system of FIG. 1. The stent constrainment mechanism 900 may be attached to the distal end 120 of the intermediate tubular member 104 and extend distally therefrom. For example, the stent constrainment mechanism 900 may include a proximal tubular portion 908 configured to be positioned within or around the distal end portion of the intermediate tubular member 104 and attached thereto. The stent constrainment mechanism 900 may include a distal opening 920 into which the stent 124 may be positioned.

As shown, the stent constrainment mechanism 900 may include a conical portion 902 that may extend distally from the distal end 120 of the intermediate tubular member 104 shown in FIG. 1. Further, the conical portion 902 may expand in a distal direction from a first diameter at a proximal end of the conical portion 902 located proximate to the distal end 120 of the intermediate tubular member 104 to a second diameter at a distal end of the conical portion 902. The conical portion 902 of the stent constrainment mechanism 900 may be configured to collapse as the distal end of the outer tubular member 102 is pressed against the conical portion 902, and likewise, the conical portion 902 may be configured to expand when freed from the outer tubular member 102.

The stent constrainment mechanism 900 may also include a necked portion 904 located distal of the conical portion 902. The necked portion 904 may have a diameter less than a more distal portion of the stent constrainment mechanism 900 distal of the necked portion 904. For example, the necked portion 904 may have a diameter less than the distal end region of the stent constrainment mechanism 900. In some embodiments, the necked portion 904 may have a diameter less than the second diameter of the conical portion 902.

The stent constrainment mechanism 900 may include a braided mesh 906 formed of a plurality of interwoven filaments or a monolithic structure. The braided mesh 906 may be formed using a suitable biocompatible material such as metal, polymer, alloy or combination of these. The multiple filaments may be bonded to each other at cross-over points using a suitable method, such as, welding, adhesive bonding, and the like, or the filaments may remain unbounded at the cross-over points, if desired.

The stent constrainment mechanism 900 may also include a polymeric membrane 912 molded to or otherwise attached to the braided mesh 906 in some instances. Similar to the polymer membrane 512, discussed above, the tubular polymeric membrane 912 may be attached to the braided mesh 906 in any desired fashion, such as molded onto the braided mesh 906 or otherwise bonded to the braided mesh 906. The material of the tubular polymeric membrane 912 may be formed of polyurethane, polyamide, silicone, and other biocompatible flexible material. In some instances, the polymeric membrane 912 may extend across or cover the proximal portions of the braided mesh 906 while the distal end portions of the braided mesh 906, such as the necked portion 904 may not be covered by the polymeric membrane 912.

Figure 10A:
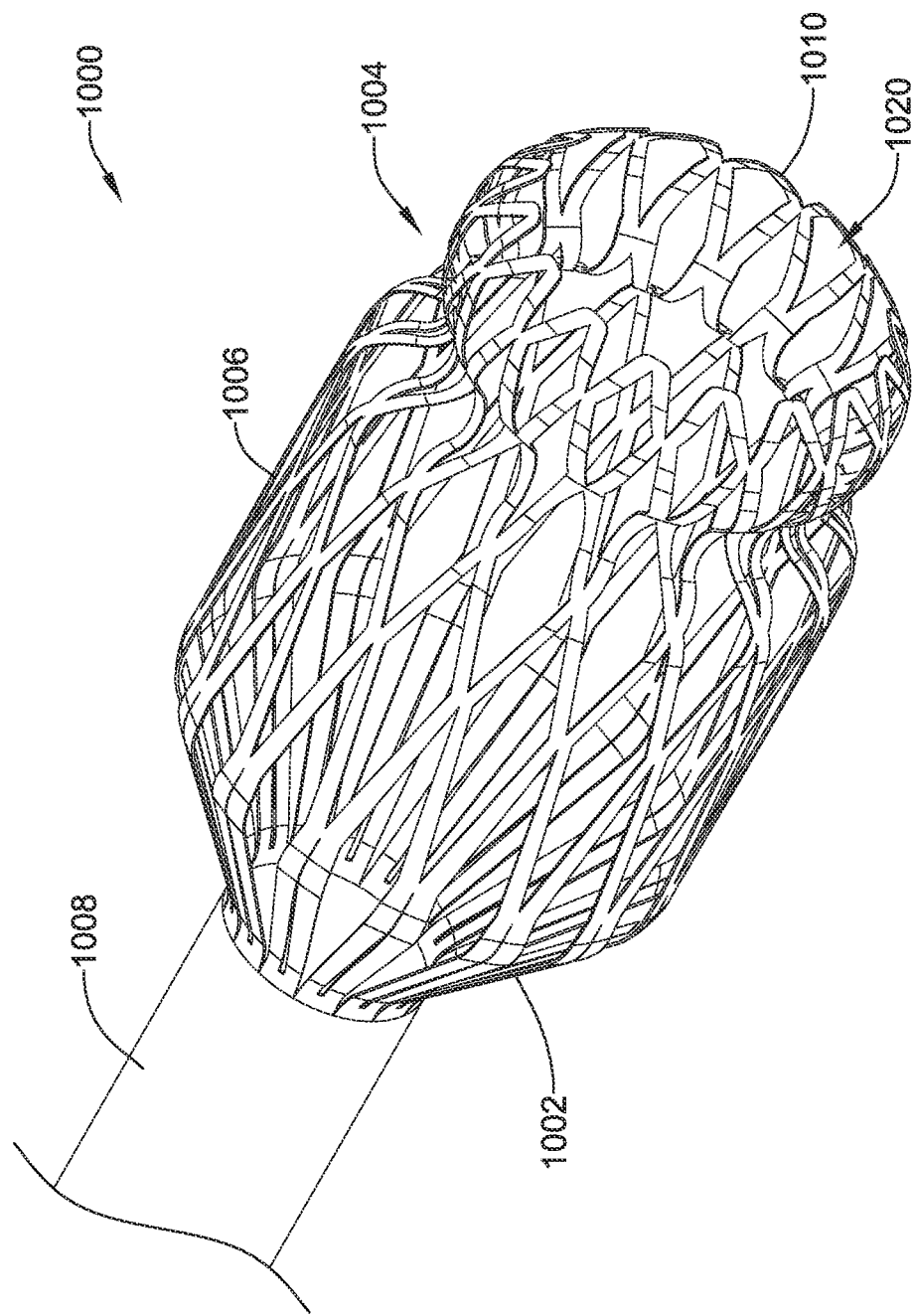
FIGS. 10A and 10B are perspective and side views, respectively, of an alternative stent constrainment mechanism for use with the stent loading and delivery system of FIG. 1.
Figure 10B:
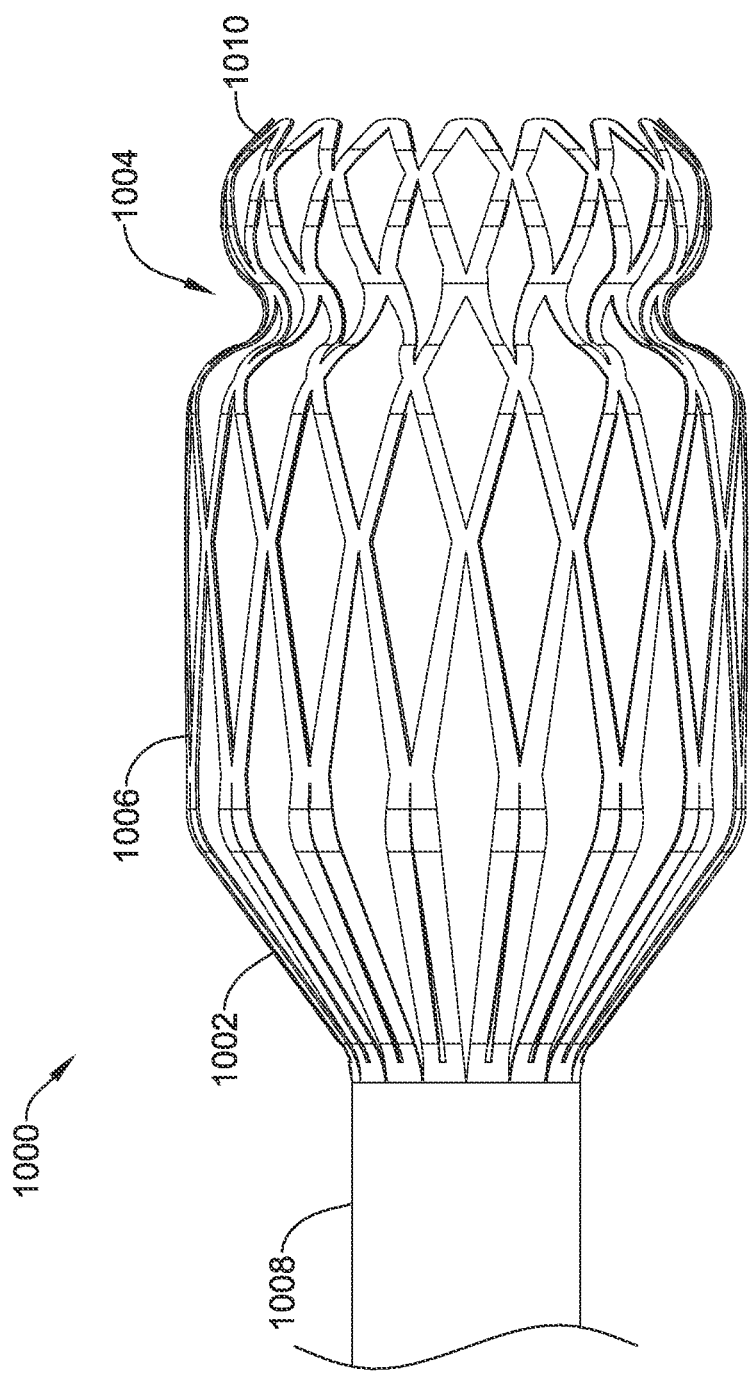

FIGS. 10A and 10B are perspective and side views, respectively, of an alternative stent constrainment mechanism 1000 for use with the stent loading and delivery system of FIG. 1. The stent constrainment mechanism 1000 may be attached to the distal end 120 of the intermediate tubular member 104 and extend distally therefrom. For example, the stent constrainment mechanism 1000 may include a proximal tubular portion 1008 configured to be positioned within or around the distal end portion of the intermediate tubular member 104 and attached thereto. The stent constrainment mechanism 1000 may include a distal opening 1020 into which the stent 124 may be positioned.

As shown, the stent constrainment mechanism 1000 may include a conical portion 1002 that may extend distally from the distal end 120 of the intermediate tubular member 104 shown in FIG. 1. Further, the conical portion 1002 may expand in a distal direction from a first diameter at a proximal end of the conical portion 1002 located proximate to the distal end 120 of the intermediate tubular member 104 to a second diameter at a distal end of the conical portion 1002. The conical portion 1002 of the stent constrainment mechanism 1000 may be configured to collapse as the distal end of the outer tubular member 102 is pressed against the conical portion 1002, and likewise, the conical portion 1002 may be configured to expand when freed from the outer tubular member 102.

The stent constrainment mechanism 1000 may also include a necked portion 1004 located distal of the conical portion 1002. The necked portion 1004 may have a diameter less than a more distal portion of the stent constrainment mechanism 1000 distal of the necked portion 1004. For example, the necked portion 1004 may have a diameter less than the distal end region of the stent constrainment mechanism 1000. In some embodiments, the necked portion 1004 may have a diameter less than the second diameter of the conical portion 1002.

The stent constrainment mechanism 1000 may include an expandable mesh framework 1006 formed of a plurality of expandable struts. In some instances, the distal end region 1010 of the expandable mesh framework 1006 distal of the necked portion 1004 may be curved or angled toward the central longitudinal axis of the stent constrainment mechanism 1000. In some instances, the expandable mesh framework 1006 may be a monolithic construction in which the expandable struts are formed from a single piece of material.

Figure 11:
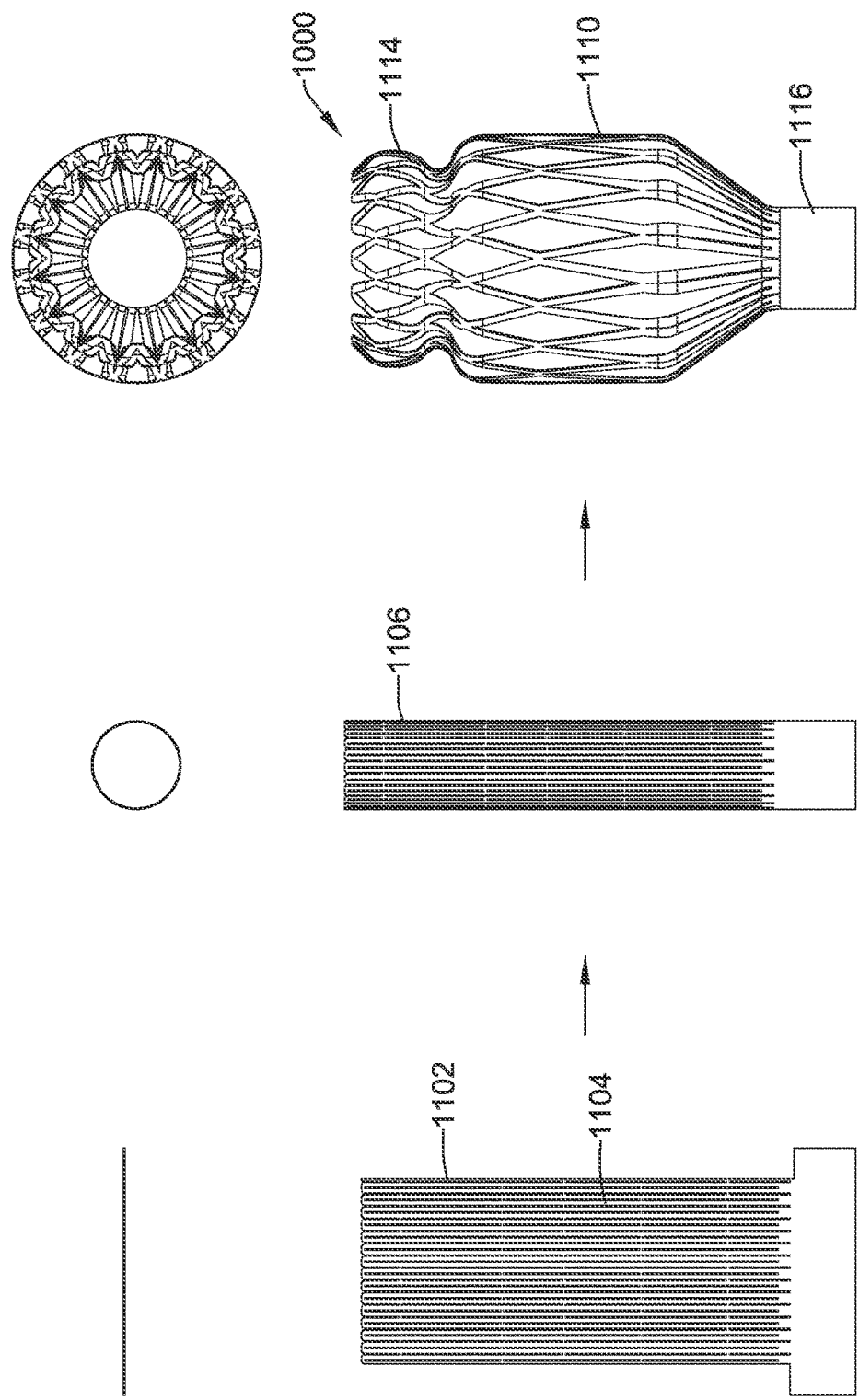
FIG. 11 illustrates an exemplary method of forming the stent constrainment mechanism of FIGS. 10A and 10B.

FIG. 11 illustrates an exemplary method of forming the stent constrainment mechanism 1000 of FIGS. 10A and 10B. In some instances, the stent constrainment mechanism 1000 can be formed from a sheet 1102 of material, such as a sheet of metallic or polymeric material. Then, multiple cuts or slits 1104 on the sheet 1102 may be formed using a suitable method such as, but not limited to, laser cutting, blade cutting, die cutting, stamping, etching, and so forth. In some embodiments, the cuts 1104 may be a combination of long and short slits, or openings formed through the thickness of the sheet of material 1102. In alternative embodiments, cuts 1104 may be longitudinal slits having a uniform length shown in FIG. 12. The sheet 1102 may be made up of suitable metal, polymer, alloy, and combination of these. Further, the thickness of the sheet 1102 may vary, as desired.

The sheet 1102 having multiple cuts 1104 may be rolled to form a tube 1106. The longitudinal edges of the sheet 1102 may be fixed together or overlapped with an overlapped portion fixed together, such as by welding or adhesive bonding, for example. The tube 1106 may define a lumen extending therethrough. A top view of the tube 1106 is shown. The stent constrainment mechanism 1000 may have a proximal end 1116 and a distal end 1114. The stent constrainment mechanism 1000 may be curved towards the distal end 1114 and may include one or more holes (not shown) at the proximal end 1116 of the constrainment mechanism 1000 for fixing or attaching to the intermediate tubular member 104. The tube 1106 then may be radially expanded, causing the adjacent struts of the mesh 1006 to expand away from one another to form the stent constrainment mechanism 1000. An end view of the stent constrainment mechanism 1000 with the expandable mesh 1006 in an expanded state is shown in FIG. 11.

It is noted that in other embodiments, the stent constrainment mechanism, such as 1000, may be formed using a tube in place of the sheet 1102. Accordingly, the cuts 1104 may be formed in the tubular member and then subjected to an expansion process, for example.

Figure 12:
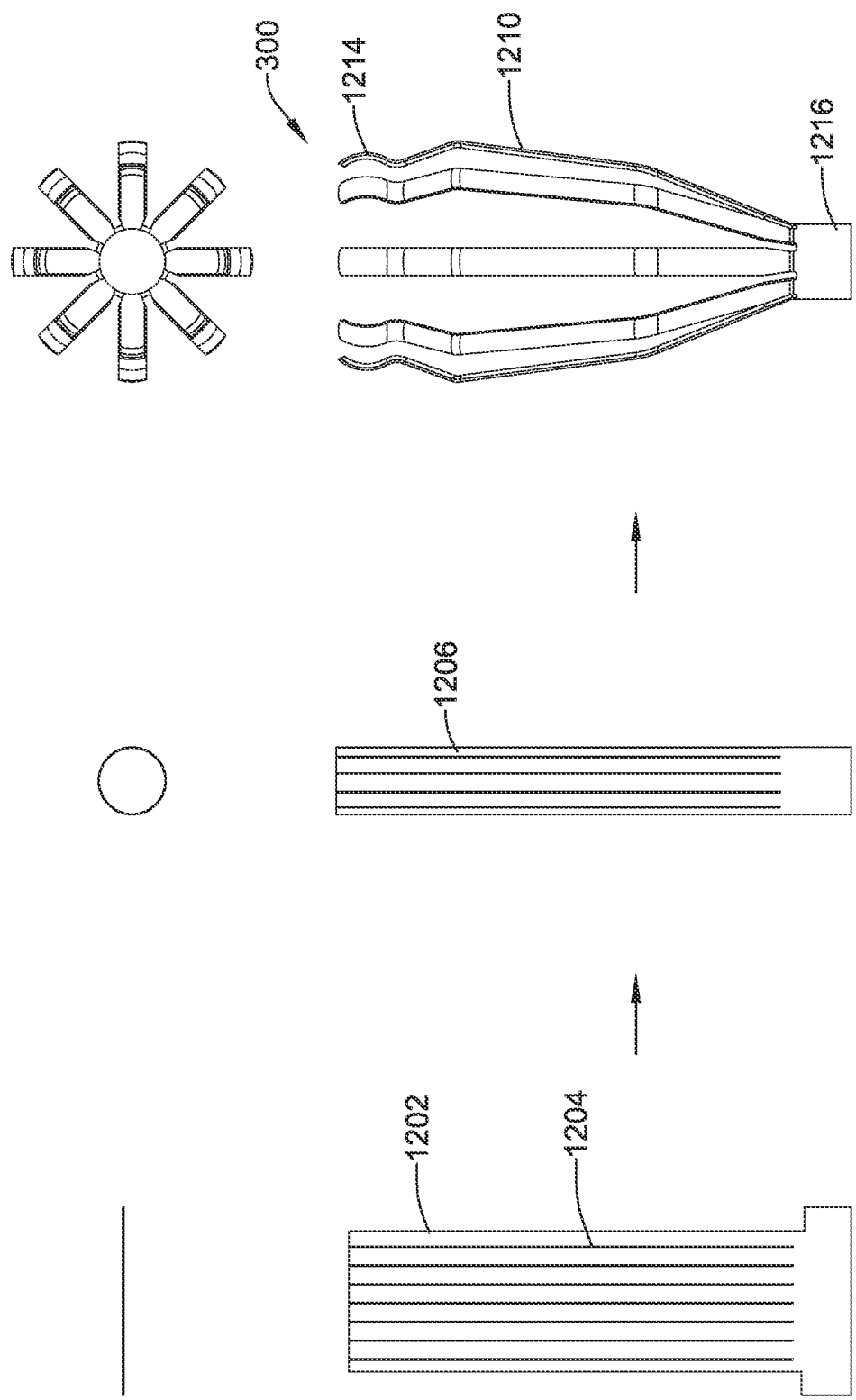
FIG. 12 illustrates an exemplary method of forming the stent constrainment mechanism of FIGS. 3A and 3B.

FIG. 12 illustrates an exemplary method of forming the stent constrainment mechanism 300 of FIGS. 3A and 3B. In some instance, the stent constrainment mechanism 300 can be formed from a sheet 1202 of material, such as a sheet of metallic or polymeric material. Then, multiple longitudinal cuts 1204 may be formed on the sheet 1202 using suitable method as mentioned above. As shown, cuts 1204 may be made longitudinally on the sheet 1202 such that the cuts 1204 divide the sheet 1202 into multiple elongate strips. Different patterns of cuts may also be formed on the sheet 1202, for example, circular, helical, and so forth, if desired. The sheet 1202 having multiple cuts 1204 may be rolled to form a tube 1206 defining a lumen extending therethrough. A top view of the tube 1206 is shown. The longitudinal edges of the sheet 1202 may be fixed together or overlapped with an overlapped portion fixed together, such as by welding or adhesive bonding, for example.

Further, the stent constrainment mechanism 300 may be curved towards a distal end 1214 and may include one or more holes (not shown) at a proximal end 1216 of the constrainment mechanism 300 for fixing or attaching to the intermediate tubular member 104. The tube 1206 then may be further processed to bend the longitudinal members 1210 formed by the cuts 1204 into a desired configuration. For example, the longitudinal members 1210 may be deformed in a press to the desired shape.

It is noted that in other embodiments, the stent constrainment mechanism, such as 300, may be formed using a tube in place of the sheet 1202. Accordingly, the cuts 1204 may be formed in the tubular member and then the longitudinal members may be subjected to a desired bending process, for example.

Figure 13A:
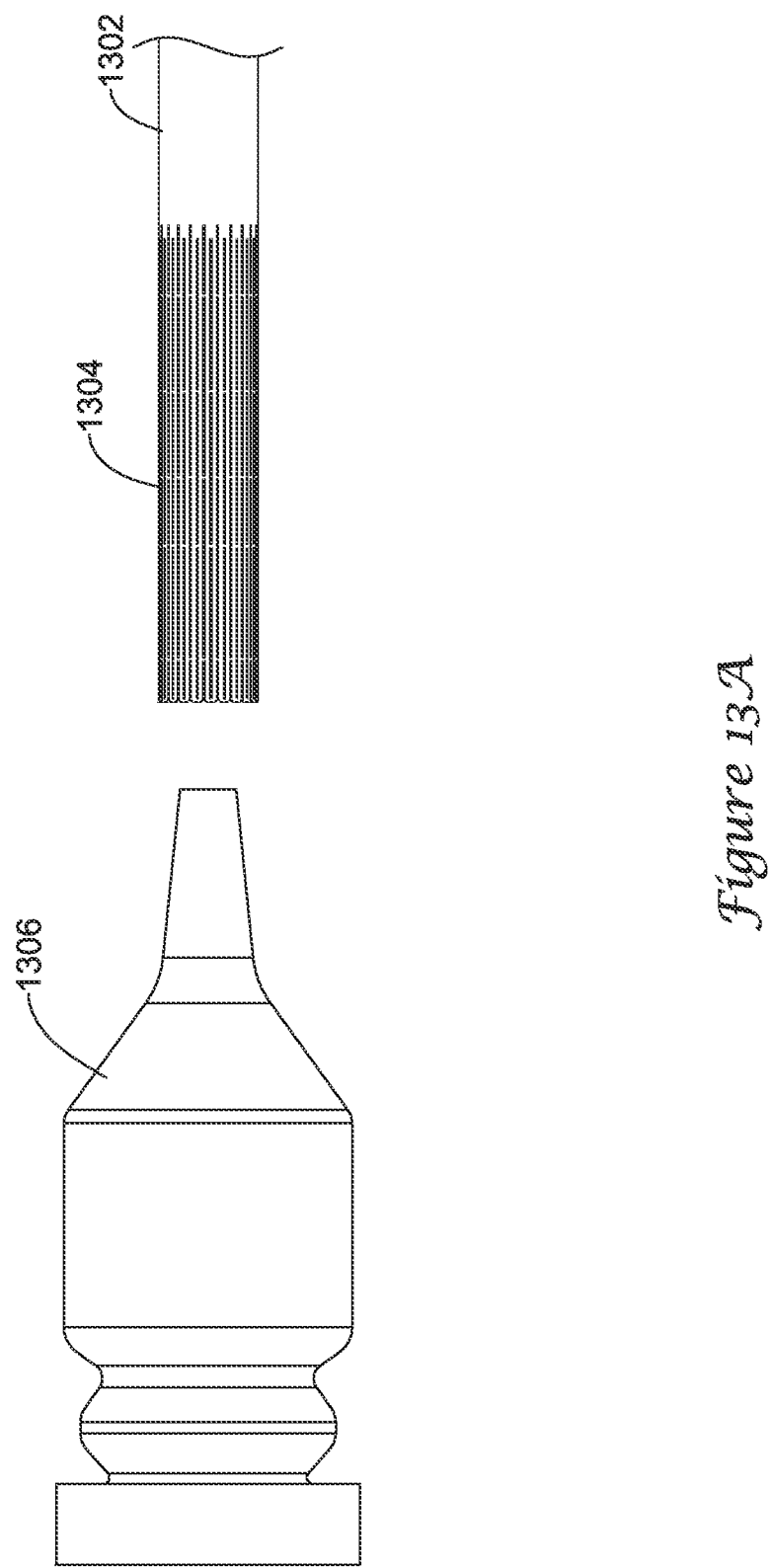
Figure 13B:
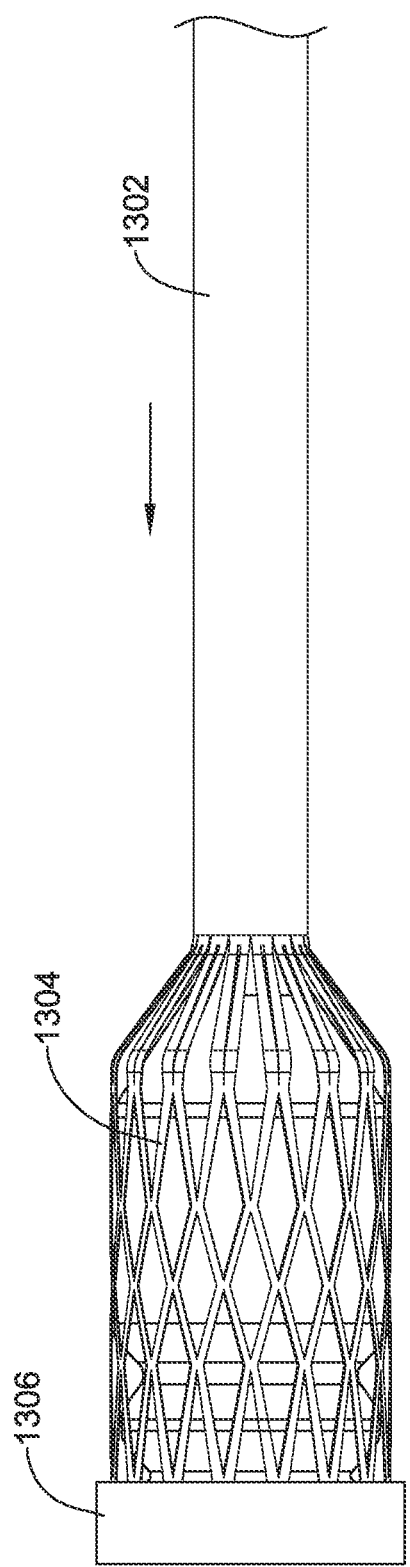

FIGS. 13A, 13B and 13C illustrate aspects of forming a stent constrainment mechanism (such as 300 or 1000). The stent constrainment mechanism can be formed using a tubular member 1302 made up of metal, polymer, alloy, and combination of these, or a sheet of material formed into a tubular member, as discussed above. Multiple cuts 1304 of a desired cut pattern may be formed on the tube 1302 using a suitable method such as laser cutting, blade cutting, die cutting, stamping, etching, and so forth. In instances, in which the tubular member is formed from a flat sheet of material, the cuts 1304 may be formed in the tubular member 1302 before or after forming the flat sheet of material into the tubular member 1302. Then a mandrel 1306, having a desired shape, may be inserted within a distal end portion of the tubular member 1302, as shown in FIG. 13B. Insertion of the mandrel 1306 into the lumen of the tubular member 1302 may radially expand the distal end region of the tubular member 1302 into an expanded state.

Thereafter, an outer shell or die 1308, such as an outer shell having a cavity with a shape complementing the shape of the mandrel 1306, for example, may be fixed over the mandrel 1306 and closed around the distal end portion of the tubular member 1302. As the die 1308 is closed around the mandrel 1306, the distal end portion of the tubular member 1302 may be shaped (e.g., compressed) to conform to the shape/contour of the outer surface of the mandrel 1306. In some instances, the die 1308 and mandrel 1306 may plastically deform the distal end portion of the tubular member 1302 into a desired shape for the stent constrainment mechanism. In some instances, the distal end portion of the tubular member 1302 may be heat set into the desired shape while being held within the die 1308. For example, after fixing or closing the outer shell 1308, the mandrel 1306 and/or die 1308 heated to an elevated temperature to heat set the distal portion of the tubular member 1302 into the desired shape. The formed stent constrainment mechanism may include a necked down portion as described above as a result of forming the stent constrainment mechanism to the contour of the outer surface of the mandrel 1306 and the cavity of the die 1308. Finally, the mandrel 1306 and the outer shell 1308 may be removed.

Figure 14A:
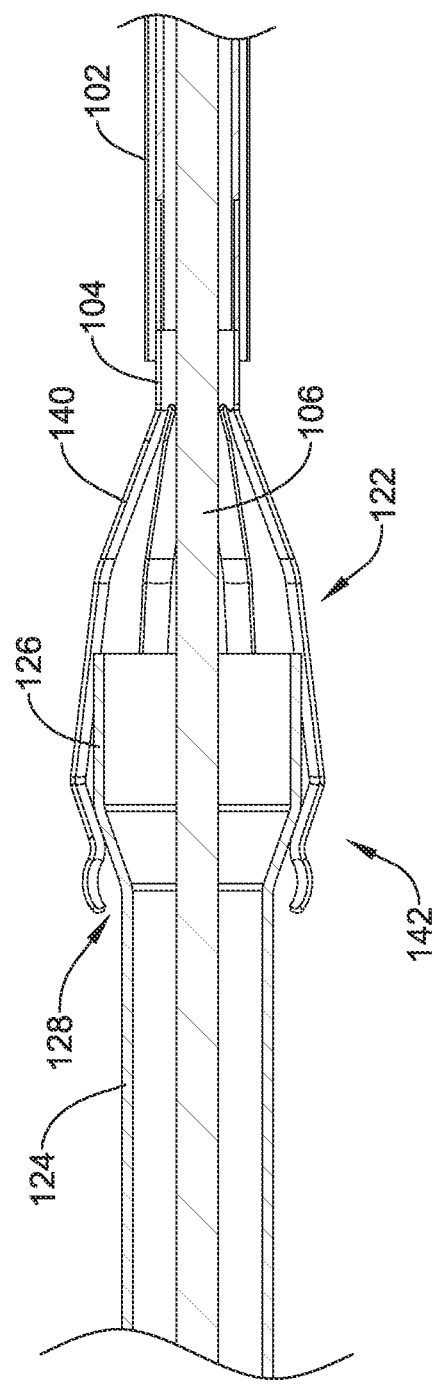
FIGS. 14A, 14B and 14C illustrate aspects of loading a stent into a delivery system using a stent constrainment mechanism.
Figure 14B:
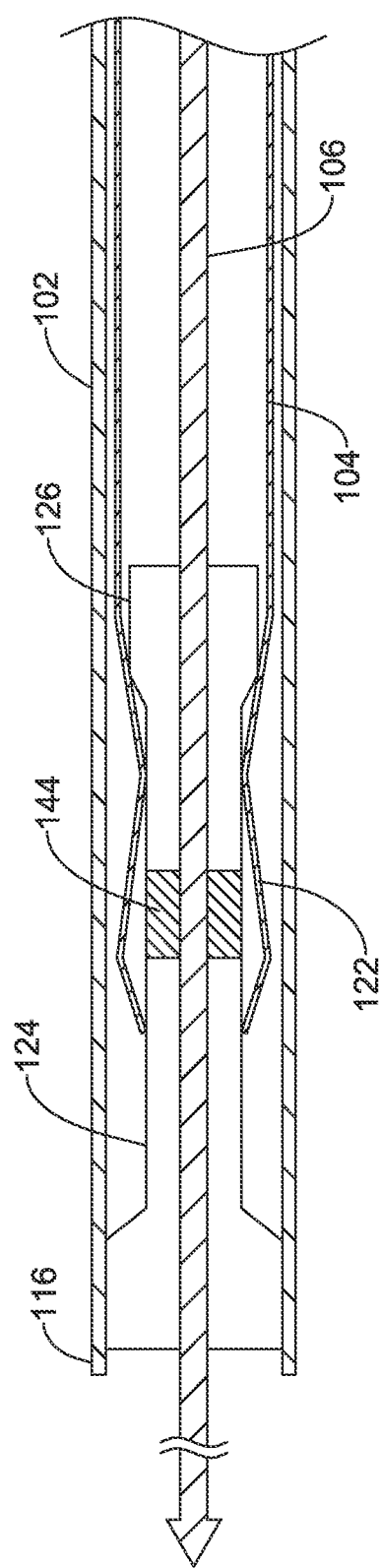
Figure 14C:
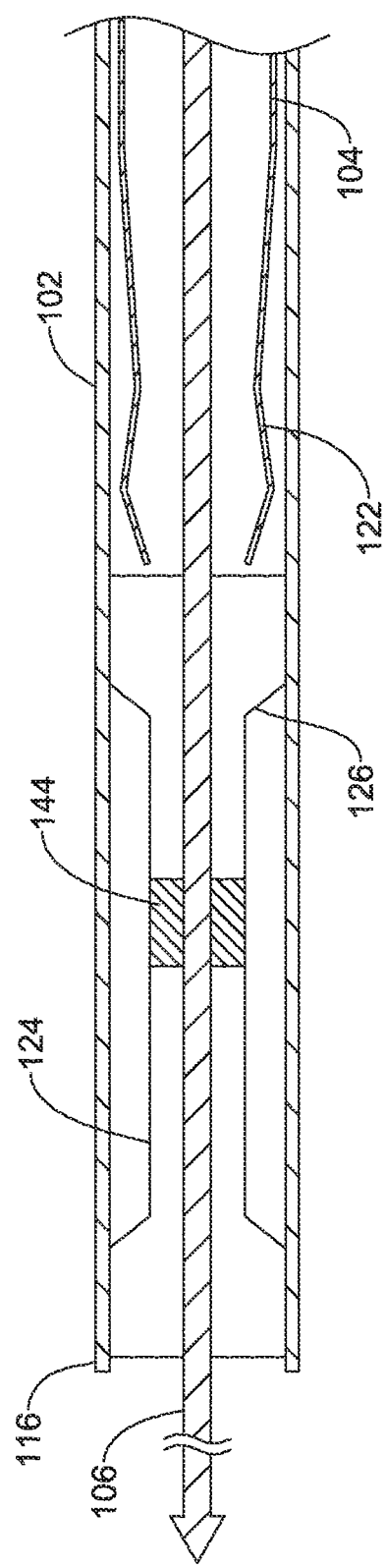

FIGS. 14A, 14B and 14C illustrate aspects of loading a stent 124 into a stent loading and delivery system 100 using a stent constrainment mechanism 122. The stent loading and delivery system 100 may be similar to the stent loading and delivery system 100 as described in FIG. 1. The stent 124 may include a proximal end portion 126 and a body portion distal of the proximal end portion 126. The body portion may have a first diameter and the proximal end portion 126 may have a second diameter greater than the first diameter of the body portion of the stent 124. The stent 124 may further include a distal end portion distal of the body portion having a third diameter greater than the first diameter of the body portion of the stent 124, in some instances.

As shown, the stent constrainment mechanism 122 may include a conical portion 140 and a necked portion 142 distal of the conical portion 140. The conical portion 140 may enlarge in a distal direction from a first diameter at a proximal end of the conical portion 140 located proximate the distal end of the intermediate tubular member 104 to a second diameter at a distal end of the conical portion 140. The necked portion 142, which may be located distal of the conical portion, may have a diameter less than the second diameter of the conical portion 140 and less than a more distal portion of the stent constrainment mechanism 122 distal of the necked portion 142.

In order to load the stent 124 into the stent loading and delivery system 100, a proximal portion of the stent 124 may be inserted into the distal opening 128 of the stent constrainment mechanism 122 in an expanded state. For example, the enlarged proximal end portion 126 of the stent 124, in an expanded state, may be inserted into the stent constrainment mechanism 122 such that the stent constrainment mechanism 122 surrounds at least the proximal end portion 126 of the stent 124. The proximal end portion 126 of the stent 124 may be positioned proximal of the necked portion 142 of the stent constrainment mechanism 122, as shown in FIG. 14A. The necked portion 142 may be configured to grab or interfere with the proximal end portion 126 to capture the proximal end portion 126 of the stent 124 in the stent constrainment mechanism 122. For example, the diameter of the necked portion 142 may be less than the diameter of the proximal end portion 126 of the stent 124 in the expanded state such that the proximal end portion 126 is captured in the stent constrainment mechanism 122 and restricted from being removed therefrom.

As shown in FIG. 14B, the outer tubular member 102 may then be disposed over the stent constrainment mechanism 122 and the stent 124 by actuating the outer tubular member 102 (or first tubular member) distally relative to the intermediate tubular member 104 (or second tubular member), and thus distally relative to the stent constrainment mechanism 122 and the stent 124. The longitudinal actuation of the outer tubular member 102 relative to the intermediate tubular member 104 may cause the stent constrainment mechanism 122 to collapse radially inward around the stent 124 to constrain the stent 124 within the outer tubular member 102. For instance, the stent constrainment mechanism 122 may collapse around the proximal portion 126 of the stent 124 by moving the outer tubular member 102 in a distal direction relative to the stent constrainment mechanism 122 and the intermediate tubular member 104 (e.g., by moving the first handle 108 in a distal direction relative to the second handle 110 and the third handle 112. Distal movement of the outer tubular member 102 relative to the stent constrainment mechanism 122 (and thus the intermediate tubular member 104) causes the distal end 116 of the outer tubular member 102 to engage the stent constrainment mechanism 122 and exert a force on the stent constrainment mechanism 122 as the stent constrainment mechanism 122 is drawn into the lumen of the outer tubular member 102. Thus, the movement of the intermediate tubular member 104 in the proximal direction relative to the outer tubular member 102 and handle 108 may cause the stent constrainment mechanism 122 to collapse radially inward due to a constraining force that is applied by the distal end 116 of the outer tubular member 102 as the stent constrainment mechanism 122 is drawn into the interior of the outer tubular member 102. As shown in FIG. 14B, as the stent constrainment mechanism 122 is radially collapsed and drawn into the lumen of the outer tubular member 102, the stent constrainment mechanism 122 may also cause the stent 124 to collapse or otherwise be constrained so that the stent 124 may be drawn into the lumen of the outer tubular member 102 as the outer tubular member 102 is moved distally over the stent constrainment mechanism 122 and the stent 124. As the stent 124 is collapsed within the outer tubular member 102, the stent 124 may engage a retention feature 144, such as a retention ring, positioned on the inner elongate member 106. For example, the inner surface of the stent 124 may be radially compressed against the retention feature 144 when the stent 124 is constrained within the outer tubular member 102. Frictional engagement between the retention feature 144 and the stent 124 may retain the stent 124 at a desired position within the outer tubular member 102.

Once the stent 124 is fully constrained within the outer tubular member 102, the stent constrainment mechanism 122 can be retracted proximally relative to the outer tubular member 102 and the stent 124 until the stent constrainment mechanism 122 is separated from the stent 124 (e.g., until the distal end of the stent constrainment mechanism 122 is actuated proximal of the proximal end of the stent 124). For example, as shown in FIG. 14C, the intermediate tubular member 104, along with the stent constrainment mechanism 122, may be actuated proximally relative to the outer tubular member 102, the inner elongate member 106 and the stent 124, to actuate the stent constrainment mechanism 122 proximal of the stent 124. For example, the intermediate tubular member 104 may be moved in a proximal direction via the handle assembly. For instance, the second handle 110 (attached to the intermediate tubular member 104) may be actuated proximally relative to the first handle 108 and third handle 112 to move the intermediate tubular member 104 proximally until the stent constrainment mechanism 122 is separated from the stent 124. The frictional engagement between the retention feature 144 and the stent 124 may prevent the stent 124 from moving relative to the inner elongate shaft 106 and the outer tubular member 102 as the stent constrainment mechanism 122 and the intermediate tubular member 104 are actuated proximally. At this point, the stent 124 may be constrained within the lumen of the outer tubular member 102, with the stent constrainment mechanism 122 positioned proximal of the stent 124. The stent 124 may then be delivered to a desired deployment location within a patient.

Figure 15A:
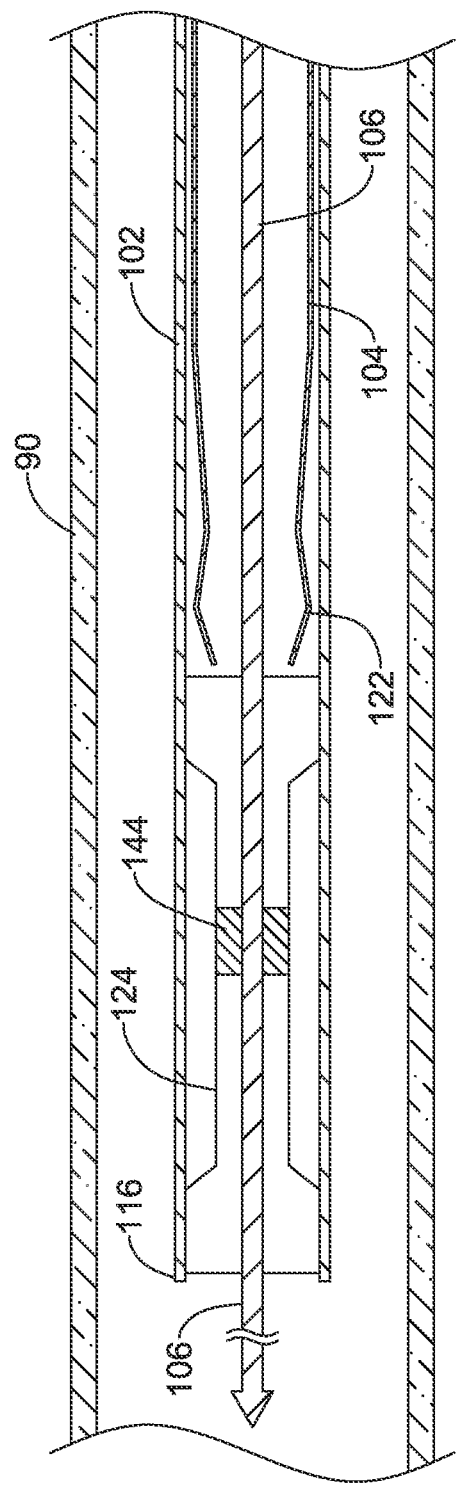
FIGS. 15A and 15B illustrate aspects of delivering and deploying a stent in a body lumen.
Figure 15B:
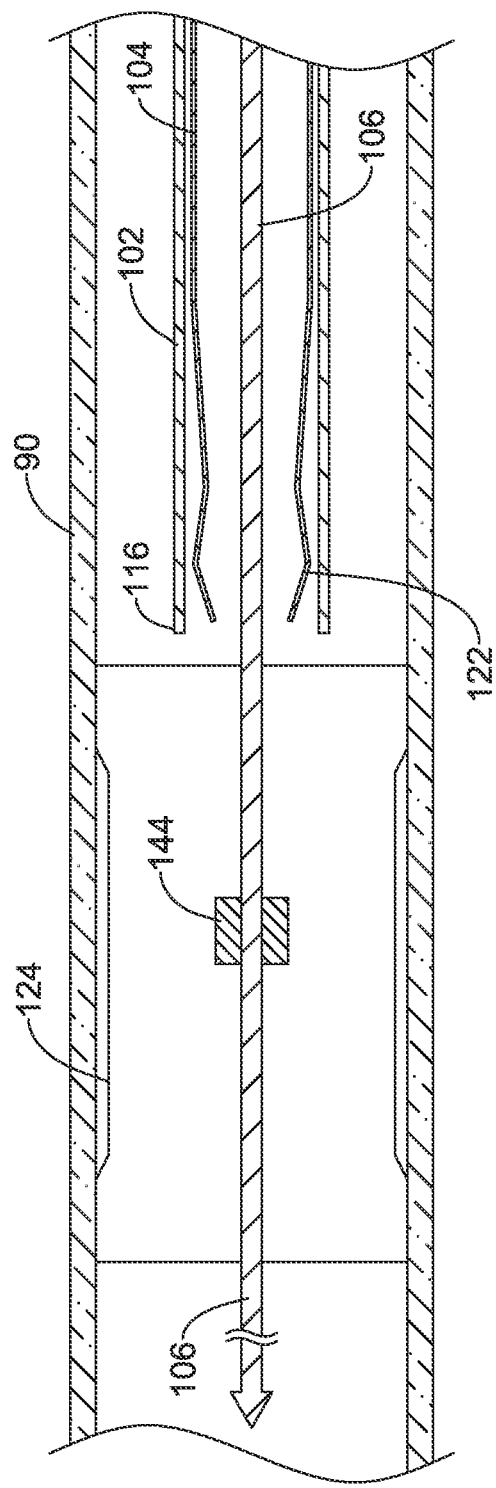

FIGS. 15A and 15B illustrate aspects of delivering and deploying the stent 124 in a body lumen 90. After loading and constraining the stent 124 onto a stent loading and delivery system 100 as described in FIGS. 14A-14C, the stent loading and delivery system 100 may be disposed or inserted in the patient's body lumen 90 following any desired access approach.

As shown in FIG. 15B, once the stent 124 has been advanced to a desired location within the body lumen 90, the outer tubular member 102 may be actuated proximally relative to the stent 124 to deploy the stent 124. For example, The handle assembly (not shown) at a proximal end of the stent loading and delivery system 100 may be actuated to move or pull the outer tubular member 102 proximally relative to the intermediate tubular member 104 and inner elongate member 106. For example, the first handle 108 (attached to the outer tubular member 102) may be actuated proximally relative to the second handle 110 and third handle 112. The frictional engagement between the retention feature 144 and the stent 124 may prevent the stent 124 from moving relative to the inner elongate shaft 106 as the outer tubular member 102 is actuated proximally. As the stent 124 is expelled from the lumen of the outer tubular member 102, the stent 124, which may be a self-expanding stent, may automatically expand towards an expanded state in the lumen of the body lumen 90. In other words, the stent 124 may automatically expand in the body lumen 90 as the outer tubular member 102 is moved proximal of the stent 124, deploying the stent 124 within the body lumen 90.

In accordance with the above disclosure, a self-expanding stent may be loaded and deployed in a body lumen using a stent loading and delivery system as described. A method of loading a stent onto a stent loading and delivery system and delivering the stent into a body lumen as described above may include a number of consecutive, non-consecutive, simultaneous, non-simultaneous, or alternative steps. The method may include inserting a proximal portion of a stent into a distal opening of a stent constrainment mechanism. The stent constrainment mechanism may include a conical portion enlarging in a distal direction from a first diameter at a proximal end of the conical portion to a second diameter at a distal end of the conical portion. The stent constrainment mechanism may also include a necked portion located distal of the conical portion. Further, the necked portion may have a diameter less than the second diameter of the conical portion. The method may also include actuating a first tubular member distally relative to a second tubular member.

The stent constrainment mechanism may be attached to a distal end of the second tubular member and the second tubular member may be disposed within the first tubular member. Upon movement of the second tubular member proximally relative to the first tubular member, the stent constrainment mechanism may be collapsed radially inward around the stent to constrain the stent within the first tubular member. The disclosed method may also include positioning a proximal end portion of the stent proximal of the necked portion of the stent constrainment mechanism prior to collapsing the stent constrainment mechanism radially inward around the stent. The stent may include a body portion distal of the proximal end portion, the body portion having a first diameter and the proximal end portion having a second diameter greater than the first diameter of the body portion. In some embodiments, the stent may further include a distal end portion distal of the body portion having a third diameter greater than the first diameter of the body portion. The necked portion of the stent constrainment mechanism may retain the proximal end portion of the stent proximal of the necked portion as the stent constrainment mechanism is collapsed radially inward around the stent to constrain the stent within the first tubular member It should be understood that this disclosure is, in many respects, only illustrative. Changes may be made in details, particularly in matters of shape, size, and arrangement of steps, without exceeding the scope of the disclosure. This may include, to the extent that it is appropriate, the use of any of the features of one exemplary embodiment in other embodiments. The disclosure's scope is, of course, defined in the language in which the appended claims are expressed.

What is claimed is:

1. A stent loading and delivery device comprising:
    a handle assembly;
    an outer tubular member extending distally from the handle assembly, the outer tubular member having a proximal end and a distal end, the proximal end of the outer tubular member attached to a first handle of the handle assembly;
    an intermediate tubular member slidably disposed within the outer tubular member, the intermediate tubular member having a proximal end and a distal end, the proximal end of the intermediate tubular member attached to a second handle of the handle assembly;
    an inner elongate member extending distally from the handle assembly within the intermediate tubular member, the inner elongate member having a proximal end and a distal end, the proximal end of the inner elongate member attached to a third handle of the handle assembly; and
    a stent constrainment mechanism attached to the distal end of the intermediate tubular member, the stent constrainment mechanism configured to receive a proximal portion of a stent into a distal opening of the stent constrainment mechanism in an expanded state, wherein upon longitudinal actuation of the outer tubular member relative to the intermediate tubular member the stent constrainment mechanism is configured to be collapsed radially inward around the stent to constrain the stent within the outer tubular member;
    wherein the stent constrainment mechanism includes a plurality of circumferentially arranged members extending distally from the distal end of the intermediate tubular member and a tubular polymeric membrane fixedly attached to the plurality of circumferentially arranged members;
    wherein the tubular polymeric membrane extends distally from the distal end of the intermediate tubular member and the plurality of circumferentially arranged members extends distally of the tubular polymeric membrane.

2. The stent loading and delivery device of claim 1, wherein the stent constrainment mechanism includes:
    a conical portion extending distally from the distal end of the intermediate tubular member, the conical portion enlarging in a distal direction from a first diameter at a proximal end of the conical portion located proximate the distal end of the intermediate tubular member to a second diameter at a distal end of the conical portion; and
    a necked portion located distal of the conical portion, the necked portion having a diameter less than the second diameter of the conical portion.

3. The stent loading and delivery device of claim 1, wherein the plurality of circumferentially arranged members extend in a longitudinal direction.

4. The stent loading and delivery device of claim 1, wherein the tubular polymeric membrane is molded to the plurality of circumferentially arranged members.

5. The stent loading and delivery device of claim 1, wherein the plurality of circumferentially arranged members includes one or more helical filaments extending distally from the distal end of the intermediate tubular member.

6. The stent loading and delivery device of claim 1, wherein the stent constrainment mechanism includes a braided member.

7. The stent loading and delivery device of claim 1, wherein the tubular polymeric membrane includes a plurality of longitudinally extending ribs.

8. The stent loading and delivery device of claim 7, wherein the tubular polymeric membrane and the longitudinally extending ribs are formed as a monolithic structure.

9. The stent loading and delivery device of claim 1, wherein the stent constrainment mechanism includes a monolithic expandable framework.

10. A stent loading and delivery device comprising:
    a handle assembly;
    a first tubular member extending distally from the handle assembly to a distal end of the first tubular member;
    a second tubular member disposed within the first tubular member, the second tubular member having a proximal end and a distal end, the handle assembly configured to actuate the first tubular member relative to the second tubular member in a longitudinal direction between a first position and a second position; and
    a stent constrainment mechanism attached to the distal end of the second tubular member, the stent constrainment mechanism configured to receive a proximal portion of a stent into a distal opening of the stent constrainment mechanism in an expanded state, wherein upon longitudinal actuation of the first tubular member relative to the second tubular member the stent constrainment mechanism is configured to be collapsed radially inward around the stent to constrain the stent within the first tubular member;
    wherein the stent constrainment mechanism includes:
        a conical portion extending distally from the distal end of the second tubular member, the conical portion enlarging in a distal direction from a first diameter at a proximal end of the conical portion located proximate the distal end of the second tubular member to a second diameter at a distal end of the conical portion; and
        a necked portion located distal of the conical portion, the necked portion having a diameter less than the second diameter of the conical portion;
    wherein the stent constrainment mechanism includes a tubular polymeric membrane molded to one or more filaments extending distally from the second tubular member, the tubular polymeric membrane having an inner diameter greater than the diameter of the necked portion;
    wherein the necked portion extends distally of the tubular polymeric membrane.

11. The stent loading and delivery device of claim 10, further comprising a stent including a body portion having a first diameter and a proximal end portion proximal of the body portion having a second diameter greater than the first diameter of the body portion.

12. The stent loading and delivery device of claim 11, wherein the stent further includes a distal end portion distal of the body portion having a third diameter greater than the first diameter of the body portion.

13. The stent loading and delivery device of claim 11, wherein the proximal end portion of the stent is positioned proximal of the necked portion of the stent constrainment mechanism.

14. The stent loading and delivery device of claim 10, further comprising a third elongate member disposed within the second tubular member and extending distally from the handle assembly, the first and second tubular members being actuatable in a longitudinal direction relative to the third elongate member.

15. The stent loading and delivery device of claim 10, wherein the stent constrainment mechanism includes a monolithic expandable framework.

16. A stent loading and delivery device comprising:
a handle assembly;
an outer tubular member extending distally from the handle assembly, the outer tubular member having a proximal end and a distal end, the proximal end of the outer tubular member attached to a first handle of the handle assembly;
an intermediate tubular member slidably disposed within the outer tubular member, the intermediate tubular member having a proximal end and a distal end, the proximal end of the intermediate tubular member attached to a second handle of the handle assembly;
an inner elongate member extending distally from the handle assembly within the intermediate tubular member, the inner elongate member having a proximal end and a distal end, the proximal end of the inner elongate member attached to a third handle of the handle assembly; and
a stent constrainment mechanism attached to the distal end of the intermediate tubular member, the stent constrainment mechanism configured to receive a proximal portion of a stent into a distal opening of the stent constrainment mechanism in an expanded state, wherein upon longitudinal actuation of the outer tubular member relative to the intermediate tubular member the stent constrainment mechanism is configured to be collapsed radially inward around the stent to constrain the stent within the outer tubular member;
wherein the stent constrainment mechanism includes at least one helical filament extending distally from the distal end of the intermediate tubular member in a first helical direction;
wherein the stent constrainment mechanism is devoid of any filaments extending distally from the distal end of the intermediate tubular member in a second direction that intersects the first helical direction.

17. The stent loading and delivery device of claim 16, wherein the second direction is an opposing helical direction.

18. The stent loading and delivery device of claim 16, wherein the stent constrainment mechanism includes a tubular polymeric membrane fixedly attached to the at least one helical filament.

19. The stent loading and delivery device of claim 18, wherein the tubular polymeric membrane extends distally from the distal end of the intermediate tubular member and the at least one helical filament extends distally of the tubular polymeric membrane.

20. The stent loading and delivery device of claim 16, wherein the stent constrainment mechanism includes:
a conical portion extending distally from the distal end of the intermediate tubular member, the conical portion enlarging in a distal direction from a first diameter at a proximal end of the conical portion located proximate the distal end of the intermediate tubular member to a second diameter at a distal end of the conical portion; and
a necked portion located distal of the conical portion, the necked portion having a diameter less than the second diameter of the conical portion.

* * * * *